United States Patent [19]
Olson et al.

[11] Patent Number: 5,682,888
[45] Date of Patent: Nov. 4, 1997

[54] APPARATUS AND SYSTEM FOR DETECTING AND LOCATING PHOTON EMISSIONS WITH REMOTE SWITCH CONTROL

[75] Inventors: Karl W. Olson, Worthington; Marlin O. Thurston, Columbus, both of Ohio

[73] Assignee: Neoprobe Corporation, Dublin, Ohio

[21] Appl. No.: 662,600

[22] Filed: Jun. 13, 1996

[51] Int. Cl.⁶ .................................................. A61B 5/00
[52] U.S. Cl. .................... 128/653.1; 128/654; 128/659; 250/336.1
[58] Field of Search .................................. 128/659, 654, 128/653.1, 662.03; 250/370.13, 370.01, 336.1, 361 K; 310/338

[56] References Cited

U.S. PATENT DOCUMENTS

| | | | |
|---|---|---|---|
| 4,782,840 | 11/1988 | Martin, Jr. et al. | 128/654 |
| 4,801,803 | 1/1989 | Denen et al. | 250/336.1 |
| 4,889,991 | 12/1989 | Ramsey et al. | 250/336.1 |
| 5,070,878 | 12/1991 | Denen | 128/659 |
| 5,158,086 | 10/1992 | Brown et al. | 128/662.03 |
| 5,351,692 | 10/1994 | Dow et al. | 128/662.06 |
| 5,441,050 | 8/1995 | Thurston et al. | 128/659 |
| 5,475,219 | 12/1995 | Olson | 250/336.1 |

OTHER PUBLICATIONS

Radioimmunoguided Surgery System Improves Survival for Patients, Bertsch, et al., Surgery 1995 118:634–639.

Radioimmunoguided Surgery in Primary Colorectal Carcinoma Arnold, et al, American J. Surg. 1995, 179:315–318.

The Significance of Intraoperative Periportal Lymph Node Schneebaum, et al. Cancer 1995; 75:2809–2817.

Identification of Occult Micrometastases in Pericolic Lymph Nodes Greenson, et al., Cancer 1994; 73:563–569.

Intraoperative Detection of Occult Colon Cancer Micrometastases Cote, et al., Cancer 1996; 77:613–620.

*Primary Examiner*—Marvin M. Lateef
*Assistant Examiner*—Eleni Mantis Mercader
*Attorney, Agent, or Firm*—Mueller and Smith

[57] ABSTRACT

A probe instrument which is formed having a unitary housing with indented switch actuating surfaces intended for surgical procedures employs internally disposed piezoelectric switching components within an elongate internally disposed switch receiving channel. The forward end of the instrument supports a crystal containing detector assembly with a preamplifier and associated leads which extend within a detector signal channel spaced from the switch receiving channel and protected therefrom by a shield wall. The piezoelectric components are held in preloaded association adjacent outwardly disposed switch actuating surfaces by a dual wedge switch support assembly. An elongate cable is permanently attached to the rearward end of the housing component through the utilization of a medical grade silicone seal and relief component.

18 Claims, 10 Drawing Sheets

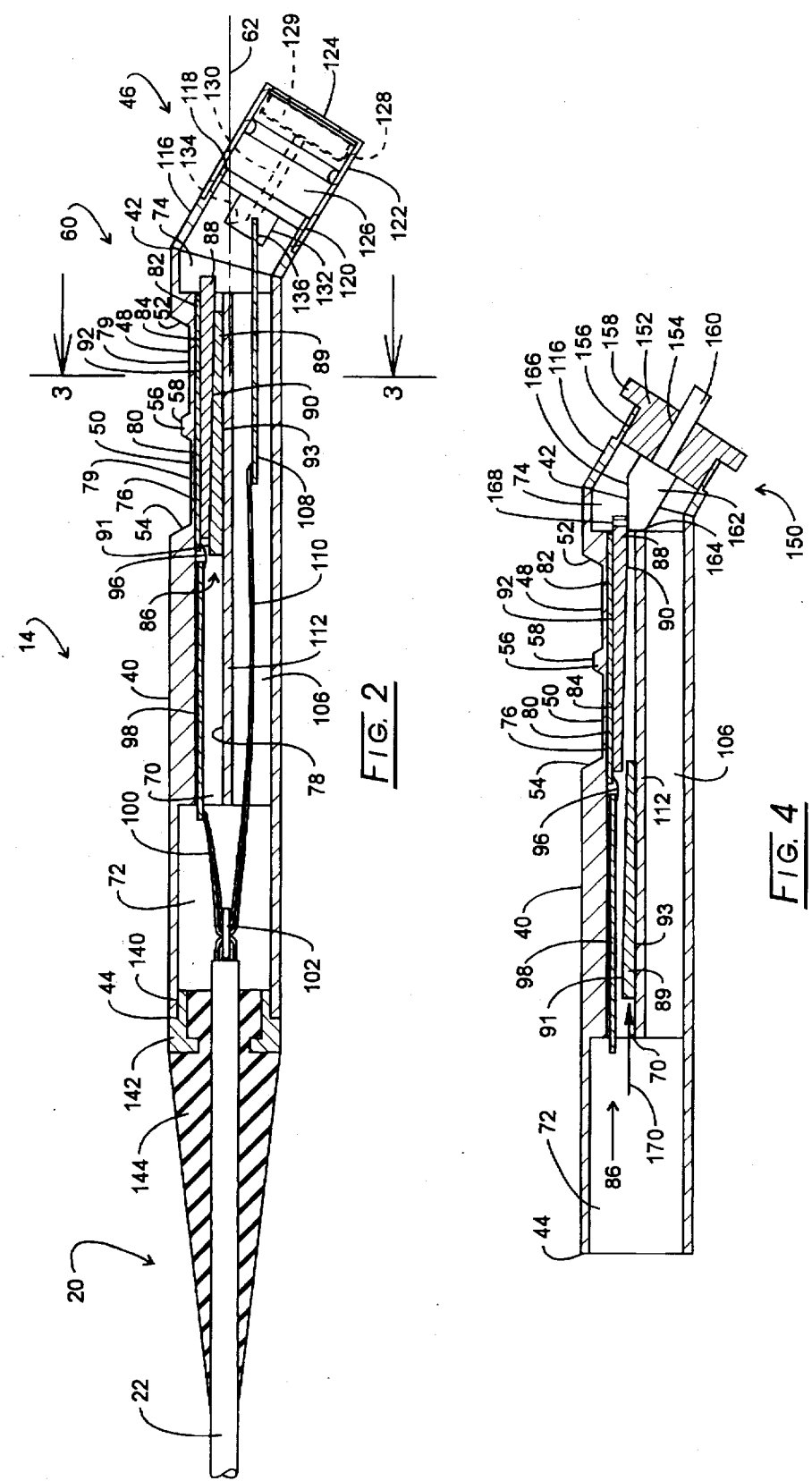

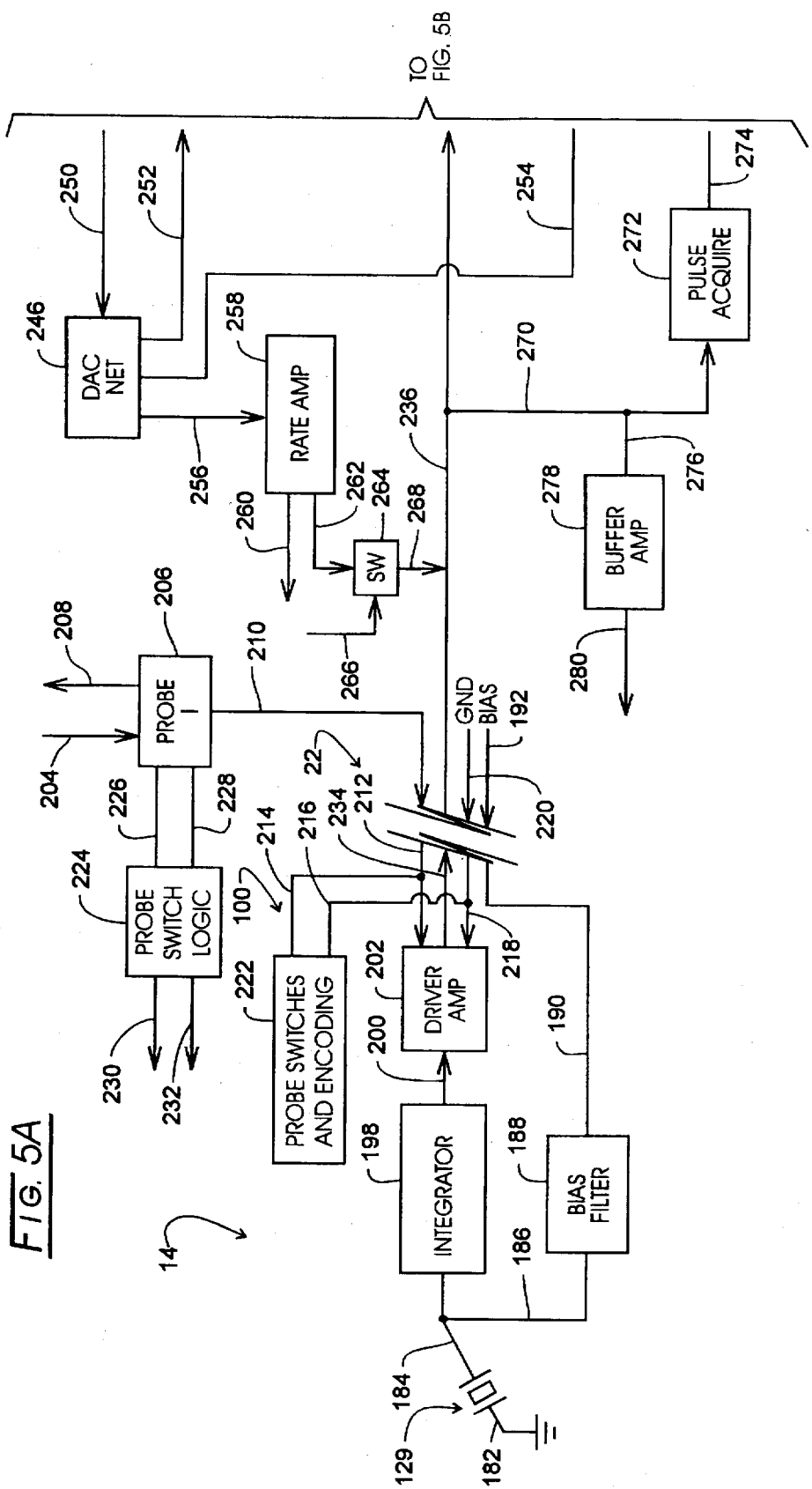

APPARATUS AND SYSTEM FOR DETECTING AND LOCATING PHOTON EMISSIONS WITH REMOTE SWITCH CONTROL

BACKGROUND

Current and historical procedures for the treatment of colon and rectal cancer generally have been based upon the natural history of tumor spread, and thence, upon operative and non-operative options available to the practitioner. Operative options generally have looked to the physical identification and surgical resection of tumor. A variety of techniques have been brought to bare in the an with the purpose of aiding the surgeon in detecting and localizing neoplastic tissue as pan of this surgical procedure. ("Neoplastic tissue", for the present purposes, often is referred to as cancerous tissue, though malignant tumor and malignant tumor cells also are found in the terminology of the art. The term "neoplastic tissue" includes all of these.) A substantial mount of effort has been expended in seeking to aid the surgeon in the process of locating neoplastic tissue has been concerned with the utilization of radiolabeled antibody. For example, one technique includes the scintillation scanning of patients who have been injected with relatively high energy, i.e. $^{131}I$ labeled antibodies. Such photoscanning or scintillation scanning provides scintigrams which are difficult to interpret because of blood pool background radioactivity. Computer subtraction of radioactive blood pool agents and the use of two labeled antibodies (one specific for the tumor and one non-specific) have been attempted in an effort to enhance imaging. Nevertheless, such techniques have been found to provide little, if any, useful information to the surgeon, especially over and above the CAT scan, magnetic resonance imaging, and like traditional techniques. Typically large tumor is readily located by the surgeon by visualization at the operating theater, and, in particular, through palpation, i.e. the feel of tumor as opposed to that of normal tissue. To achieve operative success, however, it is necessary for the surgeon to somehow locate "occult" tumor, i.e. tumor which cannot be found by the conventional surgical procedures of sight and feel. Failure to locate and remove such occult tumor generally will result in the continued growth of cancer in the patient, a condition often referred to as "recurrent" cancer. In general, conventional diagnostic techniques as, for example, use of the classic gamma camera and the like, fail to find or locate occult tumor. As tumor sites become smaller, the radionucleide concentrations at a given tumor site will tend to be lost, from an imaging standpoint, in the background where blood pool radiation necessarily is present in the patient.

In 1984, Martin, M.D., and Thurston, Ph.D., introduced a much improved method for locating, differentiating, and removing neoplasms. Such technique uses a radiolabeled antibody and a portable radiation detection probe which the surgeon may use intraoperatively in order to detect sites of radioactivity. Because of the proximity of the detection probe to the labeled antibody, the faint radiation emanating from occult sites becomes detectable, for example, in pan because of the inherent application of the approximate inverse square law of radiation propagation. The procedure now is known as radioimmunoguided surgery (RIGS®) (RIGS being a registered trademark of Neoprobe Corporation of Dublin, Ohio.) The RIGS system for surgery additionally is successful because of a recognition that tumor detection should be delayed until the blood pool background of the circulating radiolabeled antibody has had an opportunity to be cleared from the body. As a consequence, the photon emissions or radiation emitted at minute tumors compared to surrounding tissue becomes detectable in view of the proximity of the probe device to it. Fortuitously, the radiolabeled antibody is capable of remaining bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand-held probe positioned in close proximity with the tissue under investigation. The seminal patent concerned with the RIGS procedure is U.S. Pat. No. 4,782,840, by Martin and Thurston, entitled "Method for Locating, Differentiating and Removing Neoplasms", issued Nov. 8, 1988, and assigned in common herewith, the disclosure of which is expressly incorporated herein by reference.

The important advances achieved through radioimmunoguided-surgery have been reported. See in this regard, the following publications:

(1) "Radioimmunoguided Surgery system improves survival for patients with recurrent colorectal cancer" Bertsch et al. *Surgery* 1995; 118: 634–639.
(2) "Radioimmunoguided surgery in Primary Colorectal Carcinoma: An Intraoperative Prognostic Tool and Adjuvant to Traditional Staging", Arnold, et al. *American J. Surg.* 1995; 179: 315–318.
(3) "The Significance of Intraoperative Periportal Lymph Node Metastasis Identification in Patients with Colorectal Carcinoma", Schneebaum, et al. *Cancer* 1995; 75: 2809–2817.
(4) "Identification of Occult Micrometastases in Pericolic Lymph Nodes of Dukes' B Colorectal Cancer Patients Using Monoclonal Antibodies against Cytokeratin and CC49", Greenson, et al. *Cancer* 1994; 73: 563–569.
(5) "Intraoperative Detection of Occult Colon Cancer Micrometastases Using $^{125}I$-Radiolabeled Monoclonal Antibody CC49, Cote, et al., *Cancer* 1996; 77: 613–620.

The radioimmunoguided surgical system instrumentation is comprised generally of two basic components, a hand-held probe as described above, which is in electrical communication via a flexible cable with a control console. This control console is located within the operating room facility but out of the sterile field, while the hand-held probe and forward portions of its associated cable are located within that field. The hand-held radiation detecting probe is relatively small and performs in conjunction with a cadmium zinc telluride detector or crystal. Such a detecting probe is described, for example, in U.S. Pat. No. 5,070,878, by Denen, entitled "Detector and Localizer for Low Energy Radiation Emissions", issued Dec. 10, 1991, and assigned in common herewith. The somewhat remotely located control assembly or control unit provides a relatively large readout for display along with a sequence of finger actuated switches. In addition to conventional on and off switches, as well as parameter adjustment switches, the practitioner is provided a reset count switch which, upon actuation, provides an emission count readout collected over a predesignated interval. That interval typically is selected as two seconds. Additionally, the console will contain a statistical significance level selection or ranging switch which conventionally is referred to by the term "squelch". This squelch switch performs in conjunction with the above-noted reset count switch and following its actuation, a depression of the reset count switch is carried out. When this combination of two switching events occurs within a predetermined interval, the control system carries out a statistical count rate evaluation over an interval, for example, of five seconds, which functions to adjust the system to background radiation at the tissue region of current interest. In general, radiation detected from the hand-held probe initially is evaluated or validated for appropriate energy levels. Then, the validated counts representing label derived radiation are statistically evaluated in terms of count rate. Where a statistically significant count rate is encountered, the system generally operates in an aural or sound mode manifested as a siren form of output functioning to alert the surgeon that count rates have exceeded a predetermined statistical threshold. That statistical threshold is computed by the system and is referred to as a squelch threshold count rate value. The base count rate from which the threshold count rate is developed is generated by holding the crystal face of the probe against a desired region of tissue. For example, at the commencement of a surgical procedure, the probe may be held at a region of the heart for an interval of five seconds to generate an average count rate representing blood pool (background) radiation. Then the software algorithm of the control unit, depending upon its operational mode, will establish a value for the presence of tumor, for example, at a level of three standard deviations (three sigma) above the base count rate. This algorighm is described in U.S. Pat. No. 4,889,991, by Ramsey and Thurston, issued Dec. 26, 1989, entitled "Gramma Radiation Detector with Enhanced Signal Treatment", which is assigned in common herewith and is incorporated herein by reference.

The hand-held probe and its associated control unit also have found application in conjunction with procedures involving melanoma and breast cancer. In particular, such procedures look to the identification of a "sentinel" node within a regional lymph system associated with a given lesion. With this procedure, a radiopharmaceutical is injected at the site of the lesion and permitted to migrate along one or more lymph ducts toward a regional lymph node basin. The initial one and, at times, two lymph nodes to encounter this migrating radiopharmaceutical may be designated as a "sentinel" node. That node is removed for laboratory evaluation as to the presence or absence of metastasis. The RIGS instrumentation may be employed to track the draining lymph duct and then to locate the sentinel node by detecting radiation from it while positioned at the surface or skin of the patient. Through the utilization of the dual switching squelching technique described above, the body fluids. It may be observed that the probe is used within the body cavity and any mechanical joints which may fall or seams which may open or are imperfectly manufactured will result in the contamination of the probe. Switching systems pose a particular problem, inasmuch as they require a hand-actuated manipulation at some switch region with resultant flexure and, typically, with openings, albeit sealed, leading from the external surface of the probe device to its interior. The use of membrane covered switches and the like generally does not represent a desirable solution, inasmuch as the probe and associated cable should be of such robust structure as to withstand the high temperatures of autoclave-based sterilization procedures. Ideally, the housing and associated cable structure as well as any switches should be so well secure as to essentially guarantee against the incursion of body liquids in the course of surgical use.

SUMMARY

The present invention is addressed to an improved probe instrument, the method of its fabrication and a system wherein the probe instrument is employed with a remotely positioned control assembly or console. Function switching is made available at the probe itself while performing within a sterile field while maintaining its integrity against the incursion of body fluids.

The probe is structured with a unitary, integral housing component which preferably carries two finger actuated switches. This switch function is achieved without disturbing the continuous and unpenetrated structure of the housing component. In this regard, the housing component is provided as a cylinder which is machined internally to develop a switch receiving channel extending therethrough between bored cavities positioned at its forward and rearward ends. The switch receiving channel is formed having an outwardly disposed switch contact surface and an oppositely spaced apart and parallel load surface. The outer surface of the cylindrical housing is machined to define flat switch actuating surfaces parallel with and in indentation fashion over the internally disposed switch contact surface to define a predetermined switch wall thickness. A thin, flat piezoelectric switch having, for example, two switchable components, is located within the switch receiving channel such that its pressure responsive surface is located in abutment with the switch contact surface of the switch receiving channel. The piezoelectric switch or switches then are preloaded against the switch contact surface utilizing complementary wedges. With the arrangement, the surgeon readily tactilely may deriving circuit board and the circuit board, in turn, has two lead outputs which are coupled with the four lead outputs of the preamplifier at a rearwardly disposed cavity within the housing. Coupling of these wires to achieve a four wire output to an associated cable is done conveniently with a connecting circuit board within the rearward cavity.

The cable carrying these four wires is not connected to the housing through a removable connector terminal but is permanently affixed through the utilization of a cortically shaped relief component formed of a medical grade silicone.

The probe and, particularly the switching components thereof, readily are assembled. For example, a sub-assembly is made of the piezoelectric switch and an upper one of the two wedges utilized for preloading. The sub-assembly further includes the current generating circuit board which is connected with the piezoelectric switch, and two leads extending therefrom. This sub-assembly is inserted within the switch receiving channel and a simple jig is employed to position the piezoelectric switch components in registry with the switch actuating surfaces of the housing, for example through the simple expedient of two registering bores which are positioned in the forward end of the upper wedge. The lower wedge then is positioned within the switch receiving channel in conjunction with a long curing adhesive such as an epoxy. While that long curing epoxy is still fluid, the switch assembly may be tested and any adjustments necessary may be made. The forwardly disposed detector assembly with premounted preamplifier and associated four wire leads then may be attached to the forward end of the housing, preferably using a welding or alloyed soldering technique. Coupling of rearwardly extending leads within the cavity at the rearward end of the housing component then may be carded out as well as permanent attachment of the transmission cable and seal.

Other objects of the invention will, in part, be obvious and will, in part, appear hereafter. The invention, accordingly, comprises the system and, apparatus, possessing the construction, combination of elements and, arrangement of parts which are exemplified in the following detailed disclosure.

For a fuller understanding of the nature and objects of the invention, reference should be had to the following detailed description taken in connection with the accompanying drawings.

BRIEF DESCRIPTION OF THE DRAWINGS

FIG. 2 is a sectional view taken through the plane 2—2 shown in FIG. 1;

FIG. 4 is a sectional view of portions of the probe shown in FIG. 2 illustrating steps in the manufacture of a probe according to the invention;

FIGS. 5A and 5B combine as labeled thereon to provide a block diagrammatic representation of the circuits employed with the control assembly and probe shown in FIG. 1;

DETAILED DESCRIPTION

Figure 1:
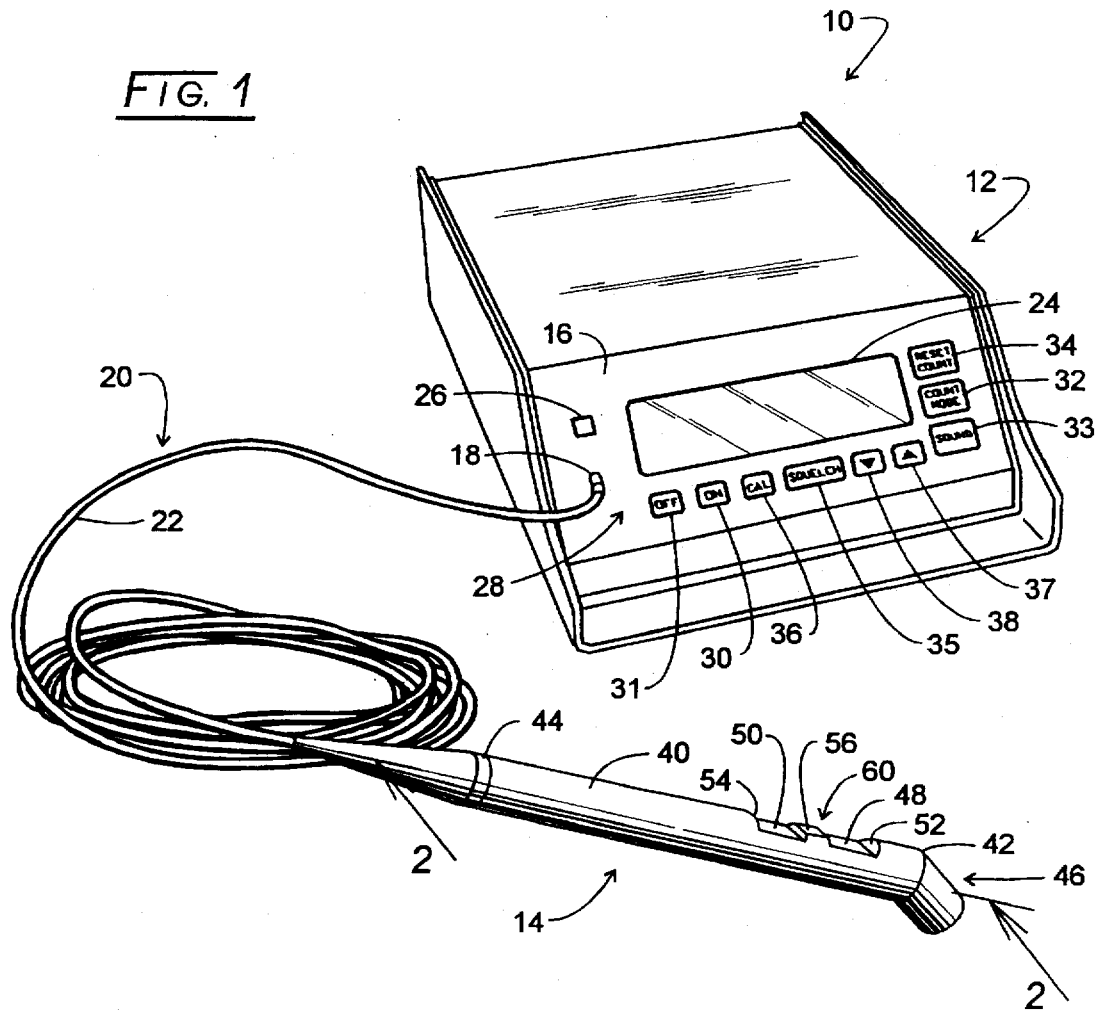
FIG. 1 is a pictorial representation of the system instrumentation of the invention.

Referring to FIG. 1, a radioimmunoguided system is represented generally at 10. System 10 includes a now somewhat conventional control apparatus or console 12 to which is coupled a probe instrument according to the invention as represented generally at 14. Apparatus 12 is described, for example, in U.S. Pat. No. 4,801,803, entitled "Detector and Localizer for Low Energy Radiation Emissions" by Denen, Thurston, and Ramsey, issued Jan. 31, 1989, assigned in common herewith and incorporated herein by reference. The forward face 16 of console 12 includes a coupling or connector 18 which provides for electrical signal communication and power supply association with the probe instrument 14 via a transmission assembly represented generally at 20, which includes a flexible cable 22. Forward face 16 of console 12 additionally carries a relatively large LCD readout or display 24, a dual colored LED readout 26, and an array of finger actuated switches represented generally at 28. This switch array 28 or keyboard permits the microprocessor driven control unit 12 to carry out an instructive or "user friendly" dialogue with the practitioner. In addition to conventional on and off switches shown, respectively, at 30 and 31, the switches provided at forward face 16 include such function selection switches as a count mode switch 32, a sound switch 33, a reset count switch 34, a statistical significance level selection or ranging switch referred to by the term "squelch" as seen at 35, a calibration switch 36, and up and down incrementing switches for adjustment within certain of the switch generated modes as shown, respectively, at 37 and 38. Of the switch array 28, reset count switch 34 and "squelch" switch 35 are employed relatively frequently during the course of use by the practitioner. The function of reset count switch 34 is to derive a count value over a preset interval, for example, 2 seconds. The squelch switch 35 is employed in conjunction with reset count switch 34 to develop a statistical count rate value based upon a measured background count rate. For example, in the RIGS procedure, the probe instrument 14 initially is positioned in the vicinity of the heart or aorta in order to obtain a blood pool background count rate. The interval during which this rate is determined is, for example, 5 seconds. The microprocessor based control system of console 12 then calculates a statistically significant value, for example a predetermined number of standard deviations of the basic background count rate to derive a statistically significant threshold radiation count rate level. This, for example, may be three sigma above the base count rate. The ranging procedure is referred to by surgeons as "squelching". Operating in conjunction with that threshold level, the system 10 provides the surgeon with audible cues indicating that a high probability of tumor involvement is present at a location closely adjacent the position of the forward window of the probe instrument 14. This squelching procedure also is utilized in conjunction with the detecting and locating of sentinel lymph nodes in connection with breast cancer or melanoma procedures. In general, the squelching procedure requires two actuations of switches at array 28. The initial actuation is that of squelch switch 35 and this is followed within a predetermined interval, for example 7 seconds, by the pushing or actuation of reset count switch 34. In general, the console 12 will be located outside of the sterile field within a surgical theater, while the probe instrument 14 will be within that sterile field and in the hand of the surgeon. It has been determined to be quite beneficial to afford the surgeon the opportunity to carry out the functions of switches 34 and 35 by the actuation of switches on the probe instrument 14 itself.

Probe instrument 14 is configured to provide a switching function emulating that provided at switches 34 and 35 while assuring its integrity against leaks from body fluids and the like. FIG. 2 shows that the probe instrument 14 is configured having a unitary housing 40 with a hand graspable surface which extends between a forward end 42 and a rearward end 44. The term "unitary" is used herein to indicate that present no joints or unions are present in the housing to establish a switching function. A detector assembly represented generally at 46 is coupled to the forward end 42 of housing 40, while transmission assembly 20 is coupled to the housing 40 at its rearward end 44. Two planar switch actuating surfaces are formed integrally into the housing 40 as shown at 48 and 50. Looking additionally to FIG. 3, it may be observed that surfaces 48 and 50 are machined into the housing 40 in a manner providing forwardly and rearwardly disposed bevels shown, respectively, at 52 and 54, which function, with the surfaces 48 and 50 to define a switching region 60. Intermediate the surfaces 48 and 50, a beveled rib 56 is defined having a flat, upwardly disposed surface 58 establishing a rib height which fails below the external periphery of housing 40. The thus-defined switch region 60 is readily tactilely identifiable to the surgeon such that region 48, carrying out the function of reset count switch 34, is easily determined by the surgeon with respect to rib 56 and bevel 52. Similarly, the surgeon readily tactilely identifies the switch actuating surface 50 by virtue of the positioning of rib 56 and bevel 54. Surgeon actuation of switch actuating surface 50 carries out an emulated switching sequence initially corresponding with the actuation of squelch switch 35 followed by an actuation of reset count switch 34. This permits the system 10 to re-establish a base count rate and threshold above that rate with a singular switch actuation as opposed to the dual actuation required at console 12.

It is a feature of the several that the unitary housing 40 is squelch function activation to progressively minimize the sound response of the system until a circle of sound is evolved of such small range as to directly locate the lymph node from which radiation is emanating. This procedure is observed to substantially minimize the extent of surgery required for lymph node analysis and that morbidity and like complications associated with conventional evaluation of metastasis involvement in such cancers.

Practitioners associated with radioimmunoguide surgery carded out with colorectal based procedures have indicated that the utilization of certain switching functions on the hand-held probe itself in addition to those on the console would be beneficial. Thus, the surgeon can carry out RIGS procedures using the hand which holds the probe rather than orally instructing a surgical assistant to carry out the switching procedures at the console which is located beyond the sterile field. However, if such switches are to be incorporated within the probe, they must be so designed as to assure that the probe interior is fully secure against the incursion of ated stress with almost no accompanying material strain. Accordingly, sealing is achieved due to the unitary nature of the construction of housing 40 without the imposition of fatigue which otherwise might evoke the presence of cracks in switching region 60 to thus permit the ingress of body fluids into the internal regions of the probe instrument 14.

Positioned in abutting adjacency with switch contact surface 76 is the pressure responsive surface 80 of a two-component thin piezoelectric switch 82. Pressure responsive surface 80 of two-component switch 82 is supported upon a stiff substrate, for example formed of FR4 material. The bottom of this material is a flat oppositely disposed support surface 84 which incorporates three terminals (not shown). With the arrangement, one switching component is located directly beneath switch actuating surface 48 and the other directly beneath switch actuating surface 50. Switches as at 82 are provided by Wilson-Hurd, Inc. of Wausau, Wis., and have been described, for example, in Iten, U.S. Pat. No. 4,857,887, issued Aug. 15, 1989. Preferably, such switches are preloaded in compression to enhance their performance.

To retain the switch 82 compressively against the switch contact surface 76, a switch support assembly shown generally at 86 is provided. Assembly 86 is formed of two complementary wedges 88 and 89 formed of aluminum with matching sloping surfaces shown, for example, respectively at 90 and 91, which serve to provide oppositely disposed parallel outer surfaces shown, respectively, at 92 and 93. Note that outer surface 93 of wedge 89 is in abutting adjacency with load surface 78 of the switch receiving channel 70. By moving wedge 89 forwardly and retaining wedge 88 in stationary position, a compressive load may be developed against the piezoelectric switch 82 serving both to hold it in position and provide a desired preloading. Accordingly, the parallel outer surfaces 92 and 93 are spaced apart a loading distance derived by the relative position between the abutting sloping surfaces 89 and 90. This support further restricts the insignificant amount of strain imposed from switch actuating surfaces 48 and 50 by finger pressure on the part of the surgeon. The two spaced piezoelectric switching devices within switch structure 82 provide a voltage categorized switching signal. Accordingly, a transmission lead is provided for each of these switches in addition to an instrument ground, such leads being connected to the noted terminals. These three leads, one of which is revealed at 96, are directed to two switch detection circuits mounted upon a circuit board 98, the combination forming an electrical transfer component. Circuit board 98 carries two current deriving circuits, one for each of the housing. Upon pressing the switch actuating surfaces, minimal flexure is caused to occur, but sufficient stress is transmitted to the piezoelectric switching components to cause a switching voltage to be generated. A detector assembly with a crystal detector is mounted at the forward end of the housing in conjunction with an associated preamplifier. This is carded out by providing a detector signal channel which extends in adjacency with the switch receiving channel through the housing component. The preamplifier and its associated wiring are extended into this latter channel. The detector signal channel is spaced from the switch receiving channel in the manner defining a shield wall to protect the preamplifier and its associated wire leads from any interference from the switching function.

The piezoelectric switch components perform in conjunction with a small circuit board mounted current deriving circuit for each switch component which also is positioned within the switch receiving channel. Three wire leads extend from the piezoelectric switch component itself to this current are configured to provide a shield wall 112 between them. Accordingly, the important signal generated at the preamplifier at circuit board 108 and the signals carried within four wire array 110 are shielded from any interference evoked from the switching components represented at switch 82 and its associated switch logic circuits at circuit board 98.

Circuit board 108 carrying the preamplifier function of probe 14 is supported from the detector assembly 46. Assembly 46 extends outwardly from forward end 42 of housing 40 as a consequence of a union of forward end 42 which is canted at an angle of 15° with respect to the centrally disposed axis 62 of housing 40 and the corresponding 15° cant of a short connector tube 116. Connector tube 116 is connected to the housing 40 at end 42 by a weld and is seen to be cylindrical in shape, and canted at 30° with respect to axis 62, open at its annular end 118. The tube 116 is necked down inwardly from the end 118 such that it may receive an end cap 122, the circular forward face of which at 124 is formed of material transparent to the radiation of interest. Connection of the cap 122 at the necked down portion 118 of tube 116 preferably is by a soldering type process employing two components which, when melted, for example by inductive heating alloy together to create a solder material generating a requisite union. Following an initial melting, that material exhibits a re-melting level above the melting point of each of the constituents and safely above autoclave sterilization temperatures. For example,indium and gold may be so combined. Also mounted upon the tube 116 is a generally cylindrically shaped detector mount 126 having a cylindrical cup-shaped cavity 128 formed therein which receives a crystal detector 129. In general, the mount 126 is formed of material attenuating radiation such as lead, and the sides of the cavity 128 extend forwardly such that only the forward face of the crystal contained therein may receive impinging radiation through window 124. In general, a cadmium zinc telluride crystal detector is employed for the instant purpose. This type of crystal requires the application of ground at its forward face immediately adjacent window 124 and the application of a bias input at its opposite or inwardly disposed surface. Such bias is applied from the preamplifier at circuit board 108 through leads extending along a cylindrical channel 130 leading to the cavity 128. FIG. 2 further reveals that the circuit board 108 carrying the preamplifier is attached to the detector mount 126 at an outwardly depending cylindrical stud 132. Stud 132 is in communication with the channel 130 which opens to reveal a conical or funnel-shaped interior configuration as shown at 134. Circuit board 108 is soldered to a slot at 136 formed in the stud 132 such that it extends rearwardly into the detector signal channnel 106 in cantilevered fashion. A preferred technique for mounting a crystal detector within the cavity at 128 as well as techniques for applying bias and ground to the crystal are described in the above referenced U.S. Pat. No. 5,070,878, by Denen.

Now looking to the transmission assembly 20, it may be observed that rearward end 44 of unitary housing 40 is connected to the necked down cylindrical portion 140 of a cylindrical rear cap 142. Connection between necked down portion 140 and the housing 40 preferably is by the dual component soldering approach employed in conjunction with cap 122 and necked down portion 120 of the detector assembly 46. Rear cap 142 is intimately coupled with an elongate conically shaped relief component 144 formed of medical grade silicone which surmounts and seals against cable 122. Such neoprene material as is used is autoclavable and such assemblies as tranmission assembly 20 are provided, for example, by Precision Interconnect Division of AMP, Inc., located at Portland, Oreg.

The assembly of the instrument 14 is substantially facilitated by the use of the switch support assembly 86 in conjunction with the switch receiving channel 70. This is accomplished even though housing 40 is of the noted unitary nature. Assembly further is facilitated by the presence of rearwardly disposed cylindrical bore or cavity 72 and forwardly disposed bore or cavity 74. Looking to FIG. 4, the assembly or fabrication procedure is illustrated in part. Assembly is commenced with the attachment of the electrical transfer component comprised of leads as at 96 and the circuit at circuit board 98 to the terminals located at the bottom of switch 82. Additionally, the electrical leads extending from the circuit at circuit board 98 which carries the switch signal treatment circuitry are attached. These two wires are depicted as lead group 100 in FIG. 2. The wires will be of a length such that they will extend beyond rearward end 44 of housing 40. Not shown in FIGS. 2 and 4 are the somewhat thin surface mounted electronics components which are mounted upon the circuit board 98. A preliminary sub-assembly is completed with the adhesive attachment of wedge 88 with piezoelectric switch 82. In general, the lower disposed support surface 84 of switch 82 is coated with an adhesive which is protected by a removable sheet of paper or plastic. That cover is removed and the switch is attached to the outer surface 92 of wedge 88. Note in FIGS. 2 and 4 that the placement of switch 82 is such that it overlaps the thinner edge of wedge 88 and exposes its thicker or forward end portion. Where the detector assembly 46 is canted at the 30° angle shown in FIGS. 2 and 4, then connector tube 116 will have been coupled to the forward end 42 of housing 40 using welding or the earlier-described soldering technique. Because such attachment may lead to variations in dimensions, it is preferred that the positioning of upper wedge 88 be mechanically referred in terms of position with rearward end 44 of the housing 40. In general, the sub-assembly comprised of piezoelectric switch 82 with wedge 88 attached thereto (A recommended practice is to assure the cleanliness of outer surface 92 of wedge 88 before attachment) and the electrical transfer component comprised of circuit 98 and its circuitry as well as leads 96 is inserted through the cylindrical bore 72 and into and through the rearwardly disposed opening within switch receiving channel 70. A fixture or jig may be provided which facilitates this positioning. However, for the arrangement at hand, the location and locking into position of wedge 88 is provided by a dual component jig type structure or fixture represented generally at 150 in FIG. 4. The jig 150 includes a cylindrical cap 152 having a bore 154 extending therethrough. The step-down cylindrical portion 156 of cap 152 is inserted within the cylindrical internal surface of connector tube 116 and its outwardly extending flange portion 158 is arranged to abut against the end of connector tube 116. Slidably inserted within the bore 154 is a cylindrical rod component 160 of a geometric jig component 162 having an abutting face 164 and an upwardly disposed surface 166, two upwardly extending pins, one of which is seen at 168 extend perpendicularly upwardly from surface 166 and are engaged with corresponding bores made in the thicker end of wedge 88. With this arrangement, the sub-assembly is properly located to position the dual component piezoelectric switch 82 beneath the switch actuating surfaces 48 and 50. The two component design of the fixture or jig 150 accommodates for the 30° cant of the combined housing 40 and tube 116. Next, the lower wedge 89 is inserted through the bore 72 and the rearwardly disposed opening within switch receiving channel 70 in the manner seen in FIG. 4. This insertion is done preferably in connection with a long curing adhesive such as an epoxy adhesive having a curing time of over eight hours. As represented by the arrow 170, wedge 89 is moved forwardly until its sloping surface 91 slidably engages the corresponding sloping surface 90 of wedge 88. While this is occurring, the wedge 88 is retained in position by the fixture 150. The wedge 89 is moved in the direction of arrow 170 to effect an abutting sliding contact between sloping surfaces 90 and 91. As the wedge 89 reaches a tight engagement, it is tapped or given a calibrated impulse by a spring loaded tamp to provide a requisite preloading of the piezoelectric switch 82 and a securement thereto in its operating position. The final orientation of wedge 89 with respect to wedge 88 is seen in FIG. 2. At this time in the assembly process, the switching function may be tested. Through the utilization of a long curing adhesive, adjustments may be made in connection with the location of the sub-assembly until its proper orientation is achieved. Following a curing interval, the fixture or jig 150 is removed by first removing the cap 152 and then the geometric jig component 162.

Detector assembly 46 then is mounted upon the connector tube 116 in the manner shown in FIG. 2. The sub-assembly comprising the detector assembly 46 includes a preamplifier 108 as seen in FIG. 2 to which four wire leads 110 are pre-attached, and those components, including wires 110 and the preamplifier circuit at printed circuit board 108 are extended as shown in FIG. 2 through the detector signal channel 106. These four wires extend as noted above to a connector circuit board 102 for connection and conjunction with the two wires at 100. The four wires of cable 22 also then are coupled to complete the assembly at circuit board 102.

In general, it is preferred that the wedges 88 and 89 be of identical configuration and a slope of 2° with respect to surfaces 90 and 92 has been found to be appropriate to achieve requisite preloading of switch 82. Because surface mounted components extend downwardly from the circuit 98, it is also necessary that the dimensioning of wedges 88 and 89 assure that no contact is made between the sloping surface 91 of wedge 89 and such components as the wedge is moved forwardly.

In prefabricating wedges 88 and 89, it is important that their complementary slopes be identical in order to assure that the outer surfaces 92 and 93 remain parallel at all times. This assures that each of the switch components at switch 82 receive substantially identical preloading and securement.

Figure 3:
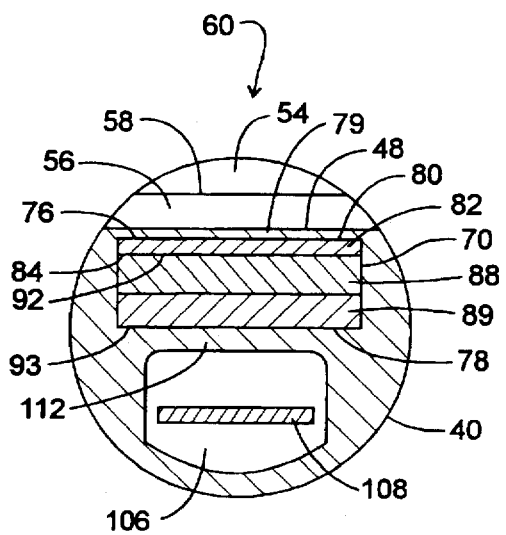
FIG. 3 is a sectional view taken through the plane 3—3 in FIG. 2.

FIGS. 2 and 3 reveal that the unitary housing 40 is configured having an internally disposed switch receiving channel 70 which is open and accessible at the rearward portion of housing 40 through a cylindrical bore-formed cavity 72 as well as from a cylindrical bore formed cavity of shorter length at the forward end as seen at 74. Channel 70 is accurately formed utilizing, for example, a wire electrical discharge machine (EDM). This permits a very accurate formation of an upwardly disposed switch contact surface 76 and a parallel planar oppositely disposed load surface 78. Each of the surfaces 70 and 78 is planar and it may be observed that surface 76 is parallel with and spaced from switch actuating surfaces 48 and 50 a predetermined distance defining a switch wail 79 of thickness selected such that flexure at the surfaces 48 and 50 under finger pressure is so minor as to be tactilely undetectable. For a preferred aluminum housing 40, that thickness will range from about 15 mils to 20 mils and resultant flexure upon switch actuation from the surfaces 48 and 50 will be in a microinch range such that, in effect, the operator is transmitting hand generated 142 and the appropriate coupling of cable 22 and relief component 144, the assembly is completed.

Figure 5B:
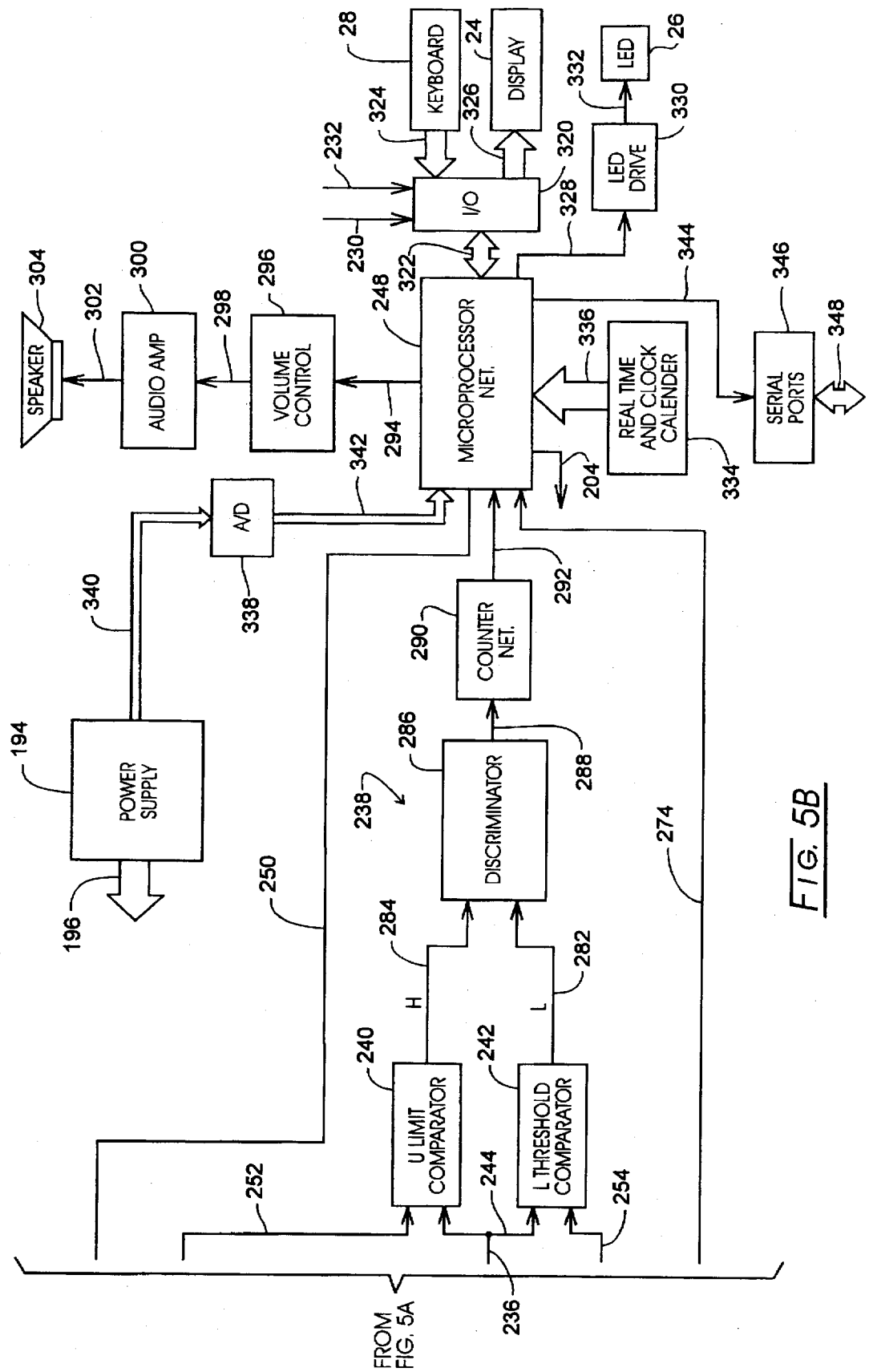

Referring to FIGS. 5A and 5B, a block diagrammatic representation of the circuitry employed with the system 10 is portrayed. These figures should be considered in mutual adjacency in the manner labeled thereon. In FIG. 5A, a crystal such as a cadmium zinc telluride crystal suited for mounting within the detector mount 126 is represented at 129 and is shown having one face coupled to ground through line 182, while the opposite, biased face thereof is coupled via lines 184 and 186 to a bias filter represented at block 188. The input to filter 188 is represented at line 190 as being applied through the cable as described earlier at 22, which number reappears in the instant figure. The bias input is seen, as represented at line 192, to emanate from a multi-output power supply shown in FIG. 5B at block 194. These various outputs are represented, in general, by an arrow 196 as seen in the latter figure. Returning to FIG. 5A, line 184 from the crystal 129, carrying detector outputs corresponding with radiation emissions impinging upon the crystal is seen to extend to an integrator stage represented at block 198. This integrator stage 198 forms part of the preamplification function mounted at circuit board 108. The integrated valuation of detected radiation emissions then is shown directed as represented by line 200 to a driver amplification network shown at block 202. A preferred preamplification circuit comprised of block 198 and 202 is described in U.S. Pat. No. 5,441,050, by Thurston and Olson, issued Aug. 15, 1995, entitled "Radiation Responsive Surgical Instrument", which is assigned in common herewith. A d.c. power supply is provided from the power supply represented at block 194 and arrow 196 (FIG. 5B) for the preamplification function. This power supply is directed, as represented at line 204, to a probe current network represented at block 206. Under microcomputer control as represented at line 208, the network 206 develops signals, for example, determining whether the probe instrument 14 has been properly connected to the console or control unit 12. Delivery of the d.c. power supply for the preamplification function is represented at lines 210 and 212. Line 212 forms a component of flexible cable 22. Connected with line 212 is one line of the output of the piezoelectric switch 82 and associated circuitry at circuit board 98 as represented at line 214. The second line of line grouping 100 is shown at 216 which is connected to instrument ground at line 218. This ground is generated from the power supply at block 194 and arrow 196 (FIG. 5B), and is represented by lines 218 and carries two current deriving circuits, one for each of the piezoelectric switch components of the switch 82. The circuits mounted upon circuit board 98 function to provide a current value superimposed upon the +12 v supply input provided to the probe 14 from the four lead cable 22. Such current signals are directed via one of the two wires of lead grouping 100 to a connector circuit board 102 mounted across cavity 72.

Located adjacent to and coextensive with switch receiving channel 70 is a detector signal channel 106 extending in open accessing relationship between cavities 72 and 74 and configured to receive a printed circuit board 108 serving to carry a preamplification circuit. This preamplification circuit associated with circuit board 108 functions in connection with a four wire lead array 110 which is seen in FIG. 2 to extend rearwardly for connection to circuit board 102. At circuit board 102, the +12 v and ground leads are coupled in common with the two wire array 100 and the four wires representing the array 110 then are extended to console 12 via cable 22. It may be observed that channels 70 and 106 signals are provided, respectively, at lines 230 and 232. For the present embodiment, the output at line 230 represents an actuation of the reset count switch and an output at line 232 represents an actuation of the squelch switch. When the squelch switch at surface 50 is actuated on probe 14, the logic in block 224 produces a sequence consisting of the assertion of a signal on line 232 followed, after a short delay, by an assertion of a signal on line 230. With the implementation of the probe switches as represented at block 222 as well as the probe switch logic represented at block 224, the pre-existing power supply line of flexible cable 22 is utilized and no additional wiring is required for that component of the system 10. This is advantageous inasmuch as it is important that the cable 22 remain as diametrically small and flexible as possible.

The preamplification stage derives count outputs which are presented along line 234 and cable 22 for introduction to the control unit 12 as represented at line 236. Line 236 extends to the input of an energy window network represented in FIG. 5B in general at 238. Looking addition to FIG. 5B, it may be observed that the energy window network 238 includes an upper limit comparator represented at block 240 as well as a lower threshold comparator represented at block 242. The count output or photon event signals at line 236 are submitted simultaneously to each of these comparator functions 240 and 242 as represented at line 244. Correspondingly, the comparison values or limits associated with the upper limit comparator 240 are applied from a digital-to-analog converter (DAC) seen in FIG. 5A at block 246. Converter 246 is under the control of the microprocessor network represented at block 248, such digital control to device 246 being asserted as represented at line 250. Thus, the upper limit value asserted at the comparator 240 is provided as represented at line 252 from DAC 246. Correspondingly, the lower threshold value for comparator function 242 is asserted from DAC 246 via line 254. Microprocessor network 248, as represented by line 250 also develops an analog signal at DAC 246, as represented at line 256, which corresponds with instantaneous pulse rate. This information is conveyed to a pulse rate amplifier network represented at block 258. The output of rate amplifier function 258, as represented at line 260, may be provided at the rear of control unit 12. The circuit represented at block 258 also may be employed to generate a calibrating pulse for testing the downstream components of the system. Thus, the microprocessor network 248 may a predetermined pulse level through the digital-to-analog conversion network 246 for presentation to the amplifier network at block 258. The resultant output at line 262 is selectively switched as represented at block 264 to provide a pulse width definition. In this regard, the switching function represented at block 264 is regulated, as represented at line 266 from microprocessor network 248, and the pulse categorized signal from switch function 264 is introduced to line 236 as represented at line 268.

The signals at line 236 also are directed, as represented at line 270, to a pulse acquire function represented at block 272. Network 272 functions, when activated by the microprocessor function 248, to acquire the value of the highest pulse amplitude witnessed at line 236. Periodically, this information then is transmitted to the microprocessor function 248 as represented by line 274. Representing a form of peak detector, the network 272 sometimes is referred to as a "snapshot circuit". Also produced from line 270, as represented at line 276 and block 278, is a buffer amplifier which will provide at line 280 an output representing received pulses which may be made available at the rearward portion of console or control unit 12 for conventional radiation evaluation purposes.

With the arrangement shown, the probe 14 assemblage derives count outputs in response to photon emissions which are confronted at crystal 129. Those count outputs will have an amplitude corresponding to the energy of interest of the photon emissions. Additionally, the signals may represent spurious phenomena such as cosmic rays and the like. Accordingly, the energies of the count outputs or amplitudes thereof are evaluated at the energy window network 238 seen in FIG. 5B. The lower threshold comparator function 242 will promulgate a pulse of fixed and consistent duration identified as "L" at line 282 when the signal asserted thereat exhibits an amplitude of value equal to or above a threshold value. That threshold value is established, as noted above, from line 254. Correspondingly, the count output signals from line 244 will be evaluated by the upper limit comparator function 240 such that when the count output signal exhibits an amplitude of value above the upper limit value established from line 252, a pulse of consistent and fixed duration identified as "H" will be promulgated at line 284. These outputs from lines 282 and 284 then are directed to the input of an asynchronous, sequential, fundamental mode discriminator circuit represented at block 286. Circuits as at block 286, while being sequential in nature, are not synchronized in any way with a clock signal. Such circuits as at 286 are described in U.S. Pat. No. 5,475,219 by Olson entitled "Validation of Photon Emission-Based Signals Using an Energy Window Network in Conjunction with a Fundamental Mode Discriminator Circuit", issued Dec. 12, 1995, assigned in common herewith, and incorporated herein by reference. The discriminator function represented at block 286 serves to generate photon event outputs for count associated signals in the form of finite pulses at line 288 upon the occurrence of a count output signal at line 236 which represents a photon emission which is valid from the standpoint of the energy range of interest associated with it. These pulses at line 288 then are counted by a counter function represented at block 290, whereupon, as represented at line 292, the count data as evaluated by the input network heretofore described is submitted to the microprocessor network 248 for statistical analysis. The function of counter network 290 may be implemented in software as described in the above-referenced U.S. Pat. No. 4,889,991. Microprocessor network 248 performs under a variety of operational modes depending upon the user inputs to the function switches 28 on the control unit 12. In general, it functions to provide outputs to two output components, one aural type generated from a speaker, and the other a visual output at display 24. Generally, a "siren" type signal manifested with a predetermined frequency variation is asserted via line 294, first to a volume control function represented at block 296, whereupon the volume adjusted signal is directed, as represented at line 298 to an audio amplification circuit represented at block 300. The circuit at block 300, in turn, as represented at line 302, drives a speaker 304. With the noted siren arrangement, the frequency output from speaker 304 increases with an exponential change from 20 Hz to 1200 Hz when the average count rate determined by system 10 exceeds a preset thresold level which is statistically significant over background count rates. The siren mode is accessed by the user either from control unit 12 by sequentially actuating squelch switch 35 and then reset count switch 34, or by applying finger pressure to the actuating switch surface 50 of probe 14. For sentinal node identification, this siren mode feature may be utilized for directing the surgeon to move the probe 14 and then carry out a squelching process by pressing the switch actuating surface 50 and reiterating that procedure until the range of movement of the probe in seeking the sentinel node based source of radiation is quite small. At that position, the resultant "circle of sound" will be effective to the extent that the window 124 will be adjacent the sentinel node and will be responding to a peak count rate. The siren mode of performance is described in detail in the above-referenced U.S. Pat. No. 4,889,991 by Ramsey and Thurston. In the RIGS general procedure, following the sequential actuation of switches 35 and 34, the count output of probe 14 is evaluated for an interval of 5 seconds to establish a base count rate. Then the program of the microprocessor network 248 establishes a predetermined statistical threshold count rate from above that base count rate such that the aural output from speaker 304 will not be present until that predetermined statistically significant count rate level is reached. Thus, by carrying out this procedure, for example at the periphery of the location of the sentinel node and then by continuing movement until the output extends from silence at the squelch location, then to sound, then to silence or a low frequency output, a sentinel node can be located both in a transverse directional sense and in the sense of depth as the probe 14 is moved into the mass of tissue in which the sentinel node is located. In the latter regard, from the generalized node carried source of radiation, the emission rate available for counting will increase in accordance with the inverse square law of radiation of propagation as the crystal detector approaches the sentinel node.

Figure 6:
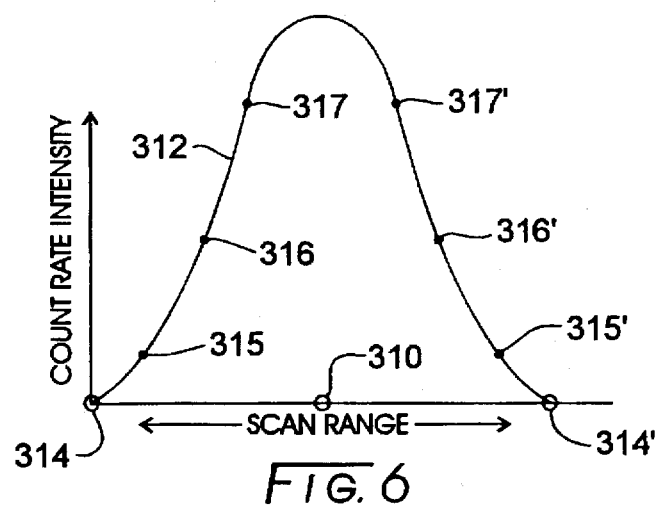
FIG. 6 is a scan range versus count rate intensity curve demonstrating a squelch based guidance technique employed with the probe of the invention.

This technique for locating the sentinel node by developing an ever decreasing squelch defined range of scan may be portrayed graphically. Looking to FIG. 6, count rate intensities during a scan over, for example, the regional node basin containing a sentinel node, is plotted against the distance the probe is moved in scanning over that region. The sentinel node, carrying a concentration of radiopharmaceutical, will be located somewhere within the tissue at the highest point of count rate intensity encountered in a scan. This midpoint is located at 310 in the drawing, and the count rate intensity may be portrayed by the curve 312. With the procedure, a conventional squelching action, i.e. pressing or actuating switch actuating surface 50 (FIG. 1 ) is carded out at a periphery of this region, for example at points 314 or 314'. The probe will be over the sentinel node midway between these points. Accordingly, the probe is moved inwardly from either of these positions as at 315 and 315', and the squelch switch actuation surface 50 is pressed to remove the sound output by elevating the squelch threshvidual pieces be permitted only along the longitudinal axis and not along their lateral axis. An acceptable fabrication of the wedges has been carded out using a single piece of aluminum wide enought for four wedge pieces. Each piece of aluminum is set-up in a milling machine and finished on one side. Then, the piece is turned over and is held down against the machine table. The surface then is machined at approximately 2° in one axis and very close to 0° on the other rectalinear axis. Then, using a slitting technique, four wedges are longitudinally cut from the singular piece of machined material. The outer surfaces of the resulting wedge pairs, with this procedure, are found to be exactly parallel within the capability of performing measurement. The machined pairs of wedges should be retained together and not mixed with pans from another machining run.

Testing again can be carried out with respect to the detector assembly 46 including the preamplifier function at circuit board 108 before the insertion of connecting circuit board 102 within the bore 72. With the connection of cap This input/output port function provides appropriate scanning of keyboard or switches 28 as represented at arrow 324. These switch inputs or function inputs are emulated by the two switching components of piezoelectric switch 82 as represented by the reoccurrence of probe switch logic output lines 230 and 232 being directed to block 320. The output port also drives the display 24 as represented by arrow 326. During a counting operation, the microprocessor network 248 functions to control a light emitting diode drive network as represented by line 328 extending to LED drive at block 330. The drive network represented at block 330 is shown providing an output, as represented by line 332, to the dual LED display as described at 26 in FIG. 1 and represented in block form with the same numeration. The readout provides a red light when a gamma ray is detected, and a green light during counting procedures. A real time clock-calendar having a non-volatile memory also may be provided in conjunction with the function of the microprocessor network 248 as represented by block 334 and arrow 336. Further, the microprocessor network 248 may be employed to monitor the performance of the power supply represented at block 194. This is shown being carried out by the interaction of the microprocessor 248 with an analog-to-digital converter represented at block 338 and having an association represented by arrows 340 and 342. As is apparent, the converter 338 functions to digitize analog values at the power supply 194 for submittal to network 248. That network also functions in conjunction with serial ports as represented at line 344, block 346, and dual arrow 348.

Figure 7:
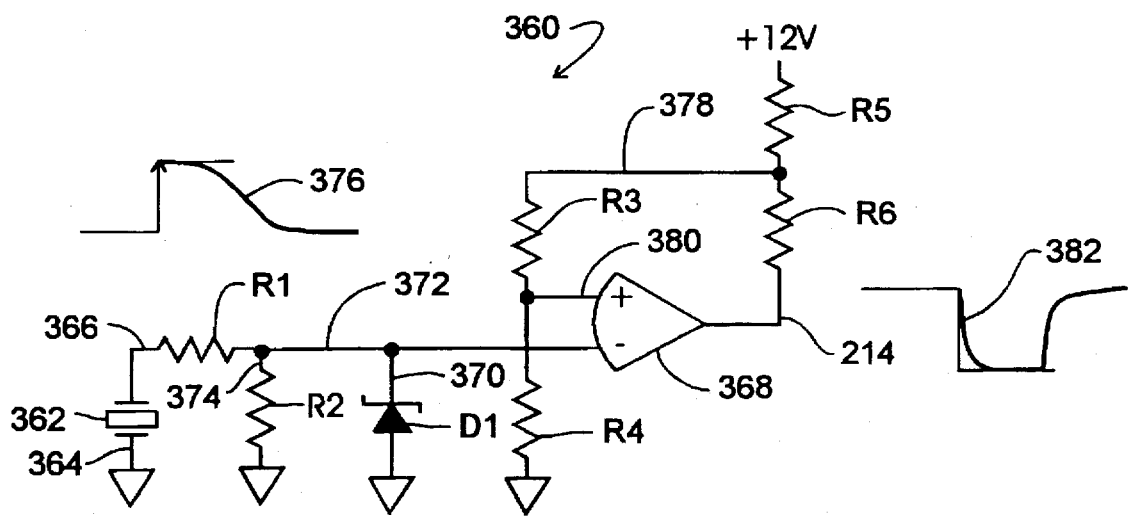
FIG. 7 is an electrical schematic diagram of a circuit employed within the probe of FIG. 2 for the purpose of generating current level signals.

Turning to FIG. 7, the circuitry by which current level signals may be transmitted along the power supply line of cable 22 from either component of the piezoelectric switch 82 is represented in general at 360. Two such circuits 360 are mounted at printed circuit board 98 described in conjunction with FIGS. 2 and 4. One such circuit provides a current level intended to cause derivation of an emulation of an actuation of reset count switch 34 (FIG. 1), and a second current level produced by an identical circuit will cause an emulation of squelch switch 35 followed by an emulated reset count switch 34 actuation. A piezoelectric component of switch 82 is represented at 362 having one side coupled to ground via line 364 and the opposite side coupled to line 366 which, in turn, is coupled with the negative terminal of an operational amplifier 368. A resistor R1 is coupled within line 366 in series with piezoelectric device 362 for providing protection against the relatively larger voltage which may be encountered should the probe 14 be dropped or otherwise physically shocked. For example, the resistor might have a value in FIG. 5A at block 222. In general, when either of the switch components of piezoelectric switch 82 is actuated, a switch voltage signal is generated which is directed to a current deriving voltage comparator circuit having an output coupled, as represented at line 214, with the power supply input line 212. The switch voltage signal generated by the piezoelectric switches, performing with the comparator circuit, functions to impose a current signal of predetermined amplitude at line 212 which is detected by probe switch logic circuitry represented at block 224. Network 224 includes monitoring amplifier stages which monitor the current excursions present at line 210 as represented by monitoring lines 226 and 228. The logic represented at block 224 includes a monitoring amplifier stage and level comparator circuit which function to provide function input signals corresponding with the actuation of either of the switch components of piezoelectric switch 82 derived by the application of finger pressure upon either switch actuating surface 48 or surface 50 (FIG. 1 ). These function input R4 is tapped at line 380 for connection with the noted positive terminal. Line 380 extends to line 214 via line 378 at a junction between two resistors R5 and R6 at the output of device 368. The ratio of resistance values for resistors R5 and R6 is, for example, 1:5, and the feedback arrangement is regenerative in order to provide a degree of hysteresis to avoid the spurious results of chattering operation or the like. In general, with the generation of the piezoelectric induced voltage represented at curve 376, a negative going curve will be produced as represented at 382 which will, over a short interval, drop from +12 v to about 0 volts to produce a pulse of current on the power supply line above the approximately 16 milliamps normally required by the preamplification function within probe 14. As noted above, a circuit essentially identical to that shown at 360 is employed in conjunction with the second piezoelectric component. In general, circuit 360, as associated with the reset count switch function is arranged to produce about 1.5 milliamperes to represent a reset count actuated signal, while the circuit associated with the squelch function will generate a pulse of current three or four times greater than that. These pulses or abrupt increases in the current flowing within the 12 v power supply line then are detected by a supplementary circuit at console 12.

Figure 8:
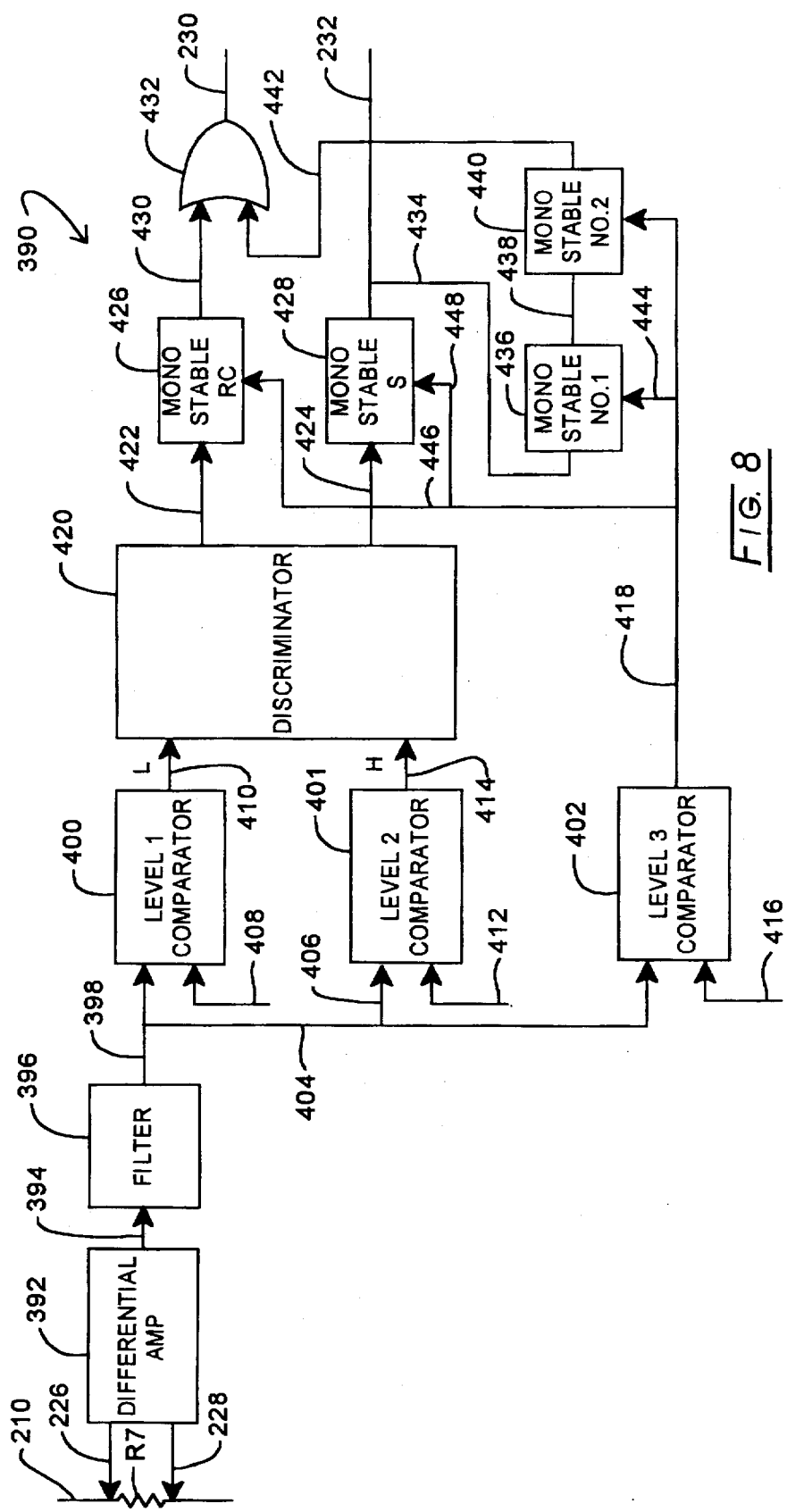
FIG. 8 is a block diagrammatic representation of a circuit functioning to develop signals emulating a reset count and squelch switch function of the control assembly shown in FIG. 1.

Referring to FIG. 8, a block diagrammatic representation of circuitry which develops the signal emulating the noted reset count and squelch switch functions is portrayed generally at 390. Circuit 390 monitors current flow within the probe current function 206 of control unit 12. In this regard, earlier described lines 226 and 228 are reproduced as monitoring the voltage induced in a resistor R7 within power supply line 210. Lines 226 and 228 extend to a differential amplification function represented at block 392. The amplified output thereof represented at line 394 is presented to a filtering form of network represented at block 396. Within this function represented at block 396, an RC circuit exhibiting a relatively lengthy time constant is employed to remove the d.c. term which generally represents current flow to the preamplification function, as opposed to the pulse categorized signals representing switching inputs. Also within the function at block 396 is an RC structured filter for blocking noise generated by bumping a piezoelectric crystal within probe 14. Without such blocking, the level comparing function of circuit 390 would be defeated. From the filter function at block 396, as represented at line 398, the voltage based pulses are submitted to three comparator stages identified as levels 1–3 and represented at respective blocks 400–402. In this regard, line 398 addresses the level 1 comparator at block 400, while the level 2 comparator at block 401 is addressed simultaneously from lines 398, 404, and 406. The level 3 comparator at block 402 is addressed simultaneously from lines 398 and 404. A threshold input to comparator function 400 is represented at line 408. This threshold is set at the lowest level and a pulse of amplitude sufficient to represent an output of that component of piezoelectric switch 82 representing a reset counter input at surface 48, will cause its triggering to provide an output at line 410, which is identified as "L". In similar fashion, a threshold input to the level 2 comparator at block 401 is represented at line 412. This upper limit as established from line 412 is selected as of higher level than that provided at line 408, such that comparator 401 will respond to generate a pulse in the presence of an actuation of the squelch identified switch actuating surface 50. In the presence of a voltage pulse of at least such upper limit amplitude, then an output will be present at line 414 which is labeled "H". It may be observed that the level 1 comparator will provide the noted "L" output at line 410 in the presence of an actuation at reset count surface 48 as well as in the presence of an actuation of the switch component at the squelch switch actuating surface 50. The level 3 comparator at block 402 receives an upper limit input as represented at line 416 which is much higher than that represented at line 412. The function of comparator 402 is to accommodate for a rapid current in-rush to the probe 14 when it is first attached to control unit 12 under the conditions where the control unit is in an on state. The output of this comparator stage 402 is represented at line 418 and will be seen to carry out an inhibit function. The level 1 and level 2 comparator outputs, at respective lines 410 and 414, are directed to the input of a discriminator circuit represented at block 420. Discriminator 420 will respond to the "L" signals at line 410 as they occur with each actuation of either of the switch actuating surfaces 48 or 50 as well as to the signal received at line 414 in response to the switch actuation from squelch designated switch actuating surface 50. The circuit then determines which probe mounted switch component has been actuated and provides an output at line 422 in the event the switch component at surface 48 has been actuated and an output at line 424 in the event that the switch component associated with surface 50 has been actuated. Preferably, the discriminator 420 is implemented as an asynchronous, sequential, fundamental mode discriminator circuit. Such circuits, while being sequential in nature, are not synchronized in any way with a clock signal. Of this circuit family, the fundamental mode form of circuits are defined as circuits with level inputs and unclocked memory elements. They are referred to as type 4 circuits as discussed, for example, in the publication: "An Introduction to Computer Logic" by Nagle, Jr., et al., Prentice-Hall, Inc., Inglewood Cliffs, N.J., 1975. The circuit at block 420 is in the preferred embodiment based upon a Mealy model wherein outputs are defined on the transitions between states as are discussed in conjunction with FIG. 10 herein. Without more, the design of discriminator circuit 420 would produce outputs at lines 422 and 424 of very short duration. Accordingly, the circuit 420 includes pulse stretching components, for example, implemented as RC networks. These networks will exhibit a time constant of approximately 1 microsecond, such that the outputs provided by circuit 420 at lines 422 and 424 will exhibit widths approximately corresponding with a duration of 1 microsecond. The outputs at lines 422 and 424 are subjected to a more extended duration pulse stretching function (100 milliseconds) as represented at respective blocks 426 and 428. The thus-stretched pulse as developed at MONOSTABLE RC block 426 is directed as represented at line 430 to a logical ORing function as represented at symbol 432. This provides an output at earlier-described line 230 which emulates the actuation of reset count switch 34. The output of pulse stretching MONOSTABLE S 428 is presented at earlier-described line 232 which is reproduced in the instant figure. This will provide an initial emulation of an actuation of squelch switch 35 at line 232. The output at line 232 also is directed via line 434 to the input of a monostable multivibrator identified as "MONOSTABLE NO. 1" and represented at block 436. Device 436 functions to interpose a delay, following which an output is presented at line 438 which is directed to a monostable multivibrator identified a "MONOSTABLE NO. 2" and represented at block 440. The device represented at block 440 creates a pulse of equivalent width with that generated at line 430 and presents it via line 442 to the ORing function 432. With this arrangement, the control unit 12 will respond to an emulated actuation of switch 35 and then switch 34 to cause the system to enter a siren mode and carry out a base count over an interval, for example, of five seconds whereupon a count rate threshold of statistical significance is established above the rate represented by that base count.

Returning to the level 3 comparator function at block 402, where a noted very high amplitude pulse is received which is well above the limit established at the level 2 comparator function at block 401, then an inhibit signal is presented at line 418 for a preset duration selected to occur throughout such high amplitude pulse. This signal functions to inhibit the operation of the monostable multivibrator functions represented at blocks 436 and 440 as represented by lines 418 and 444. Additionally, the pulse stretching functions represented at monostable blocks 426 and 428 are inhibited as represented by lines 418, 446, and 448.

Figure 9:
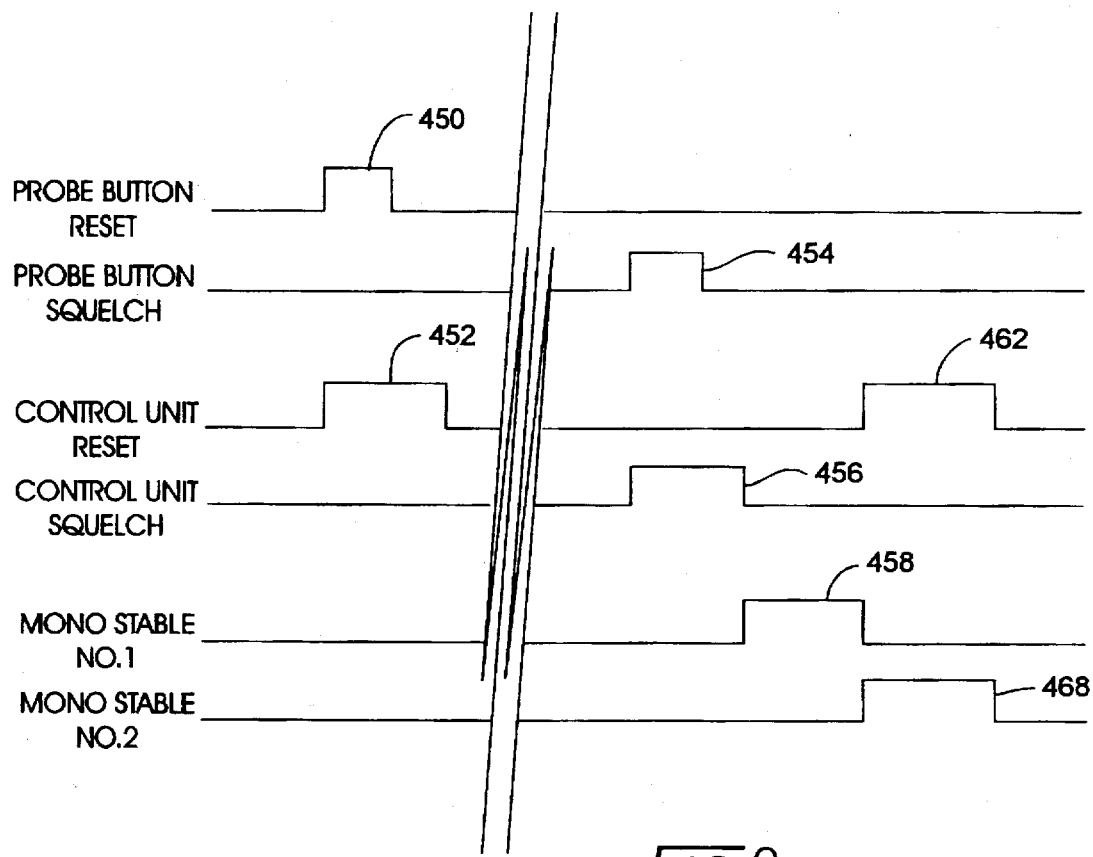
FIG. 9 is a pulse output diagram illustrating the performance of the circuit of FIG. 8.

Looking to FIG. 9, a signal or pulse output diagram showing the performance of circuit 390 is set forth. In the figure, the pulse output at line 422 corresponding with the actuation of reset counter switch 34 is represented at 450. The corresponding pulse directed from line 230 within the control unit 12 is shown as a pulse 452 which has been subjected to the pulse stretching function 426. The actuation of the squelch switch 35 will create a pulse at line 424 which is represented at 454. This will create a corresponding pulse at line 232 emulating the actuation of squelch switch 35 and shown as a pulse 456. The falling edge of pulse 456 will trigger monostable multivibrator No. 1 represented at block 436 to provide a delay interval represented as a pulse 458. The falling edge of pulse 458, in turn, triggers monostable multivibrator No.2 represented at block 440 which derives a pulse of fixed and known duration represented at 460, which is directed to the OR function 432 to provide that same pulse as a reset counter switch emulation shown as pulse 462, thus causing control unit 12 to enter a base counter and count rate threshold setting mode of operation.

The asynchronous, sequential, fundamental mode discriminator circuit described in conjunction with block 420 in FIG. 8 may be described in conjunction with a state diagram. For this application, this circuit was designed with four states, a–d, however, one such state for the present circuit will never be entered and is not utilized in the diagram to follow. Such a diagram is presented in FIG. 10 with three stable states, a–c, and employing the nomenclature "L" representing the signal at line 410 and "H" representing the signal at line 414. When these signals are present, they are identified by a logic 1, in their absence, they are identified by a logic 0. It may be recalled that the signal "L" is reproduced by the actuation of either the reset count switch at old. Note that the range now has narrowed and the probe still will be over and pointing down toward the sentinel node when it is over the midpoint 310. The surgeon again may move the probe inwardly, for example, to location 316 or 316' and again carry out the squelching procedure. A subsequent scan between those points again is one of narrowed range to bracket the location of the midpoint 310 over the sentinel node. A squelching procedure again may be carried out by moving the probe inwardly from the last point of squelching, for example to scan between points 317 and 317'. Such a scan will show a very narrow circle of sound. At this juncture, only slight movement of the probe is required to complete a traverse and the location of the sentinel node readily is determined. This same procedure then is carried out in terms of three-dimensional movement through an incision toward the sentinal node.

Returning to FIG. 5B, microprocessor network 248 performs in conventional fashion with an input/output network as represented at block 320 and dual directional arrow 322.

output from level 2 comparator 401, then a transition represented by transition arc 480 occurs at the termination of the pulse with the corresponding output from the discriminator function of 1,0. This condition then may be represented as $\overline{LH}$/10 as labeled upon the arc 480. The circuit then will have returned to stable state a as represented at circle 470 and an output transition to 0,0. Where the signal under evaluation is crossing both the lower threshold of comparator 400 and the upper limit of comparator 401, a transition occurs for the condition LH/00 as represented by transition arc 482. As represented by transitional loop 484, the resultant stable state c then ensues. Because the pulses under evaluation will exhibit falling edges, the conditions represented at transitional loops 486 and 488 for respective conditions $L\overline{H}$/00 and $\overline{L}H$/00 are present. However, with the presence of the condition $\overline{LH}$/01, then the transition represented by transition arc 490 obtains and state a is entered as represented at circle 470.

Figure 10:
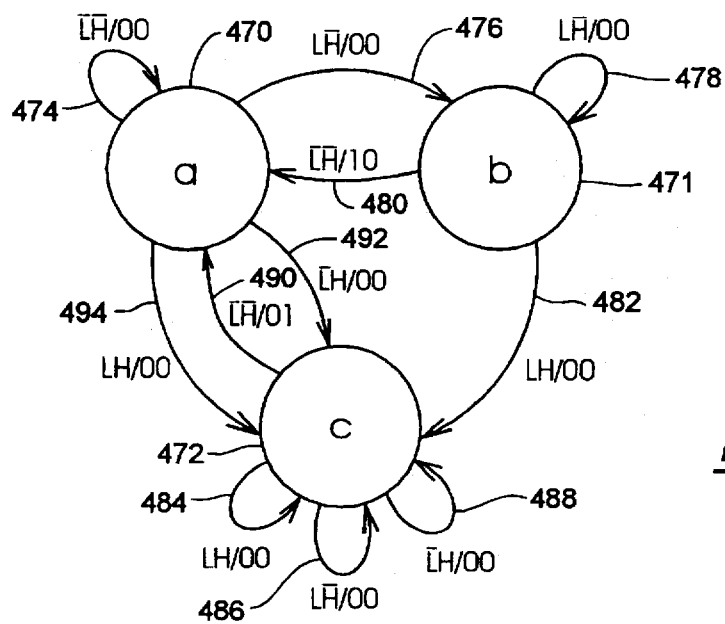
FIG. 10 is a state diagram illlustrating the performance of a discriminator circuit shown in block form in FIG. 8.

The state diagram of FIG. 10 additionally shows other possible logic events and results therefrom. For example, the presence of the condition $\overline{L}H$/00 in connection with state a will result in the transition represented by transition arc 492 providing a transition to state c. Similarly, the condition LH/00 occurring in state a will result in a transition to state c as represented at transition arc 494. Based on the foregoing, the implementation of the discriminator circuit 420 may take a variety of forms depending upon the desire of the designer. For instance, the diagram can be implemented by programming in conjunction with an electronically programmable logic device (EPLD), for example, a type EPM5130 marketed by Altera Corporation of San Jose, Calif. Alternately, more simple circuits may be employed using conventional semi-conductor logic devices. A further analysis of the circuit developed in conjunction with discriminator function 420 is described and illustrated in a copending application for United States patent entitled "Remotely Controlled Apparatus and System for Tracking and Locating a Source of Photoemissions" by Thurston and Olson, Ser. No. 543,032, filed Oct. 13, 1995, and assigned in common herewith.

Further analysis of the state performance leading to the circuit of FIG. 8 may be carried out, for example, employing a modified primitive flow than assigning conditions for L and H, an implication table determining whether conditions of the chart may be eliminated, a resultant reduced flow chart and assignment map wherein measurable variables are assigned to the arbitrary states a, b, and c. With such a map, of about 100,000 ohms. A Zener diode D1 coupled within line 370 between line 372 and ground also provides surge protection. A next resistor R2 coupled within line 374 between line 372 and ground provides a path for d.c. bias current. Resistor R2 also has a relatively larger value, for example 50 megaohms and develops a time constant with the capacitance associated with device 362 of relatively lengthy value. In this regard, when the piezoelectric switch is actuated, a voltage which may be represented by curve 376 is generated. The device 362 will generate a voltage, for example, as high as about 6 volts. The output of amplifier device 368 is present at line 214 (see FIG. 5A). Line 214, in turn, is coupled to the +12 v power supply conveyed from the control unit 12 to the probe 20 along relatively lengthy cable 22. Cable 22, for example, may have a length of 12 to 15 feet. Device 368 is configured as a comparator and, accordingly, the positive terminal thereof is coupled to a voltage divider circuit including resistors R3 and R4 coupled within line 378. The union between these resistors R3 and Referring to FIGS. 11A–11D, an electrical schematic representation of the circuit of FIG. 8 is presented. These figures should be considered in the mutual orientations as labeled thereon. Where appropriate, common identifying numeration is employed between FIG. 8 and FIGS. 11.

Figure 11A:
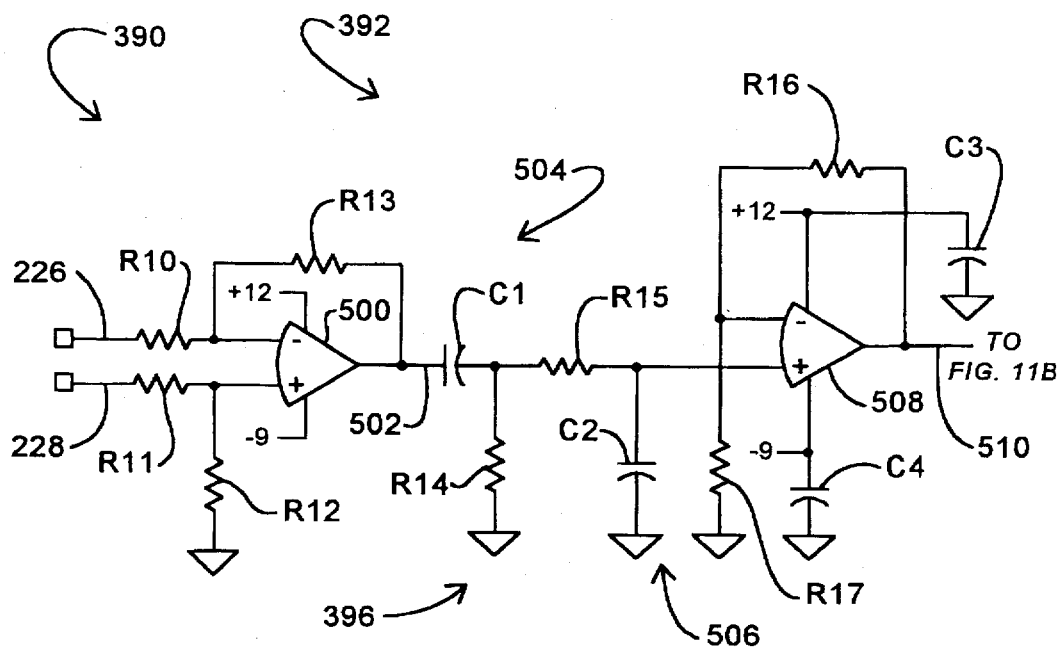
FIGS. 11A–11D combine as labeled thereon to provide an electronic schematic diagram of the circuit shown in FIG. 8.

Looking to FIG. 11A, the amplification and filtering functions described earlier at blocks 392 and 396 are illustrated. Lines 226 and 228 are connected across the earlier-described resistor R7 and are directed with respective resistors R10 and R11 to the respective negative and positive inputs of a differential amplifier 500. Lines 226 and 228 as well as amplifier 500 are configured with resistors R10–R13 to provide a voltage division of the incoming d.c. signal and to provide a gain of about 2.5. Device 500 may be provided, for example, as a type TL072 and derives an output at line 502. A benefit of this circuit configuration is that the nominally 12 v common mode voltage present on both lines 226 and 228 is reduced to approximately 9 v at the two inputs of device 500, a level which can be accommodated by that device. Because the d.c. term of incoming signal at lines 226 and 228 represents the current draw of the preamplification stage in probe 14, an RC network 504 including capacitor C1 and resistor R14 is provided to filter the noted d.c. term out through the utilization of a very long time constant, for example, of about 4.7 seconds. This long time constant avoids undershoot phenomena which would have derogatory effects at the comparison stages. Cascaded with the RC circuit 504 is another RC circuit 506 comprised of resistor R15 and capacitor C2. Network 506 exhibits a much shorter time constant, for example 0.01 seconds, and functions to filter high frequency signals which may be be generated when the cadmium telluride crystal 123 of the probe 12 may be shocked by bumping or the like. Because of its piezoelectric nature, such spurious signals may be encountered which would otherwise trigger the downstream circuitry. The network 506 also provides beneficial filtering of extraneous noise.

From network 506, output line 502 extends to the positive input terminal of a conventional, non-inverting amplification stage including amplifier 508. Device 508, which also may be of a type TL072 is configured with resistors R16 and R17 to provide a gain of 28 at its output line 510, which will be present as a negative-going pulse when either component of piezoelectric switch 82 is actuated.

Figure 11D:
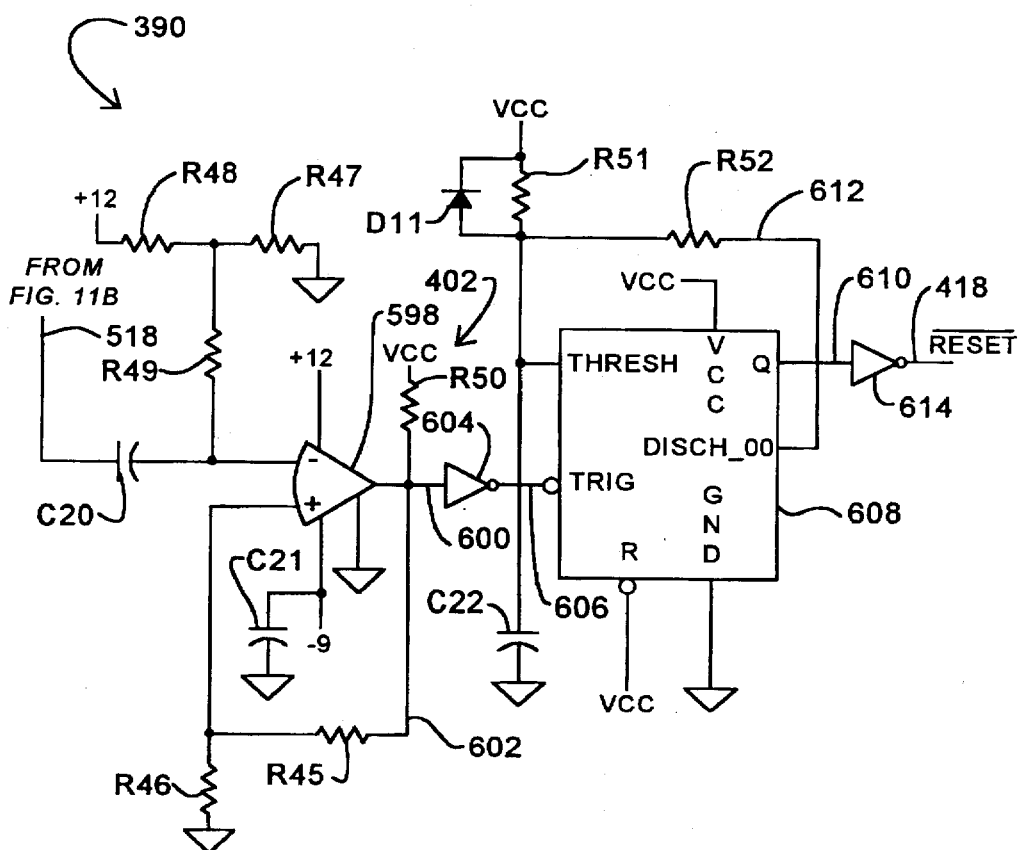
Figure 11B:
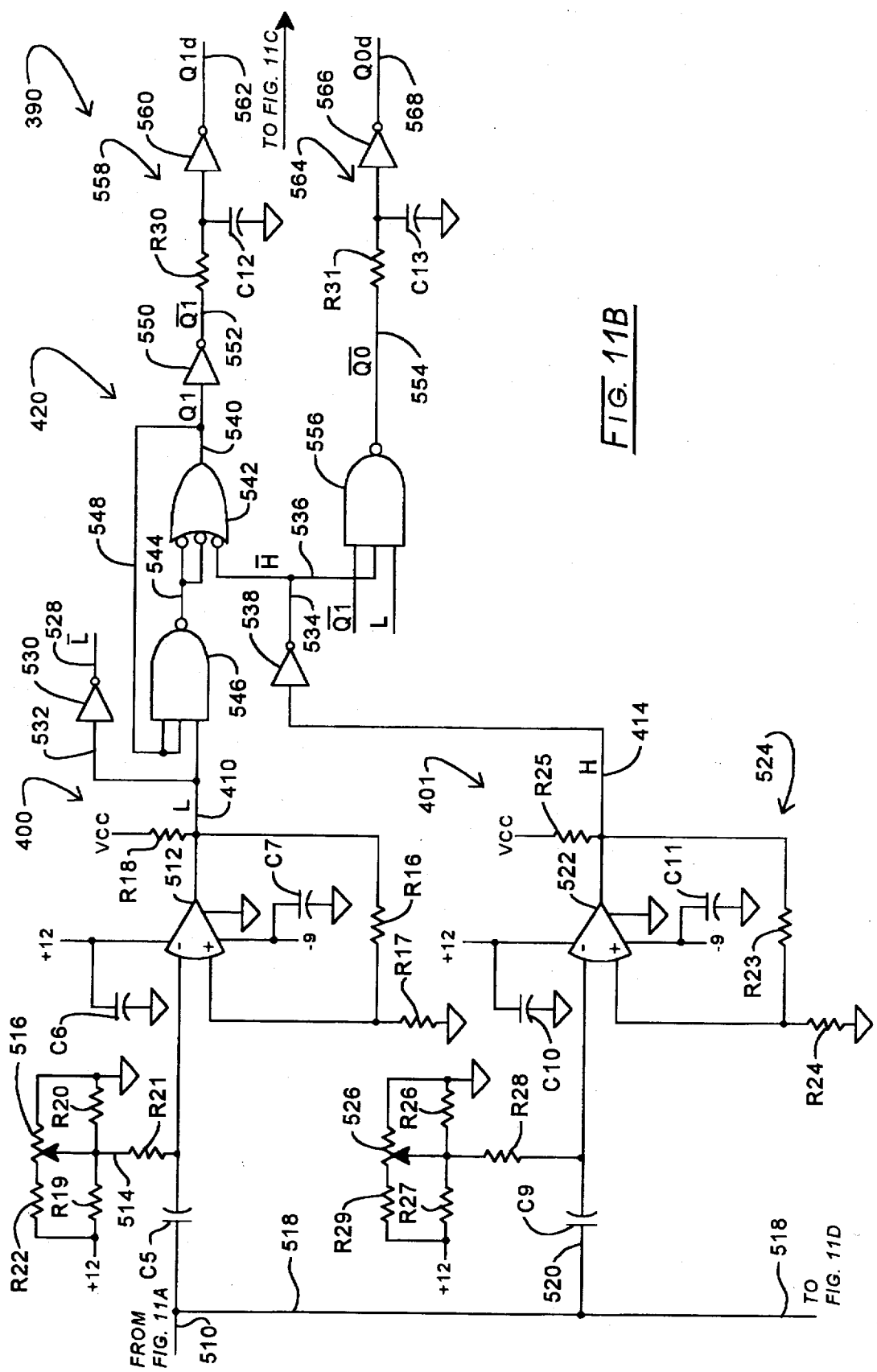

Looking to FIG. 11B, line 510 reappears introducing this negative-going pulse signal to level 1 comparator stage 400 and level 2 comparator stage 401. In this regard, line 510 incorporates coupling capacitor C5 which is directed to the negative input terminal of comparator 512. Having an output at line 410, the comparator may be of a type LF311 which is configured with power decoupling capacitors C6 and C7, and includes a feedback path to a positive input terminal incorporating resistors R16 and R17, thereby providing a hysteresis characteristic for circuit 400. A pull-up resistor R18 is coupled between output line 410 and Vcc. The threshold limit response for this comparator stage 400 is derived by fixed resistors R19–R21, which are coupled to input line 510 via line 514. In this regard, resistors R19 and R20 are coupled between +12 v and ground. As an alternate configuration, a resistor R22 in combination with a manually adjustable potentiometer 516 may be substituted in place of resistors R19 and R20. Resistor R21 functions to couple the bias-like voltage developed from resistors R19 and R20 into the negative terminal of comparator 512. As is apparent, a time constant is evoked with respect to coupling capacitor C5 and resistor R21. The resultant inverted signal at line 410 is a positive going transition earlier labeled "L". The signal at line 510 simultaneously is directed via lines 518 and 520 to comparator stage 401. Stage 401 includes a comparator 522 which is configured with capacitors C10 and C11 as well as hysteresis resistors R23 and R24 within feedback path 524. A pull-up resistor R25 is coupled between its output line at 414 and Vcc. As before, the negative going input pulse from line 510 is coupled to the negative input terminal of device 522 through capacitor C9. The threshold level or upper limit of stage 401 is established, as before, either by resistors R26–R28 or by resistor R28 performing in conjunction with fixed resistor R29 and manually adjustable potentiometer 526. As before, the resistors R26 and R27 are coupled between +12 v and ground as would be resistor R29 and potentiometer 526 were they to be employed.

The L and H outputs at respective lines 410 and 414 are directed to the discriminator circuit 420. Circuit 420 is configured to carry out the logic discussed in conjunction with FIG. 10. In this regard, $\overline{L}$ is generated at line 528 by virtue of the coupling of line 410 to the input of an inverter 530 through line 532. Correspondingly, $\overline{H}$ is developed at lines 534 and 536 from line 414 which is directed to the input of an inverter 538.

The LH outputs at respective lines 410 and 414 are directed to the discriminator circuit 420. Circuit 420 is configured to carry out the Boolean logic discussed in conjunction with the four equations above. In this regard, $\overline{L}$ is generated at line 528 by virtue of the coupling of line 410 to the input of an inverter 530 through line 532. Correspondingly, $\overline{H}$ is developed at lines 534 and 536 from line 414 which is directed to the input of an inverter 538. The variable Q1 is developed at line 540 which is the output of an ORing function 542 receiving the $\overline{H}$ variable from line 536 as well as the output at line 544 of a NAND function 546, the input to which receives the L variable from line 410 as well as the output at line 540 via line 548. This Q1 variable at line 540 is inverted at inverter 550 to provide the variable $\overline{Q1}$ at line 552. The $\overline{Q0}$ variable is developed at line 554 as an output of NAND function 556, the inputs to which are the $\overline{H}$ input at line 536; the $\overline{Q1}$ input developed at line 552; and the L variable from line 410.

To avoid short output durations of signals at lines 422 and 424 (Fg. 8) due, for example, to the Mealy transitional output, a pulse stretching delay of approximately one microsecond is generated within lines 552 and 554. In this regard, an RC network 558 formed of resistor R30 and capacitor C12 is provided at line 552, whereupon the delay signal is inverted at inverter 560 to provide the signal Q1d at line 562. Similarly, an RC network 564 is provided in line 554 which is formed of resistor R31 and capacitor C13. The delay signal is inverted at an inverter 566 to provide the signal Q0d at line 568. It may be noted that since these pulse stretching delays are outside of the feedback loop (line 548), implementing the fundamental mode circuit 420, the dynamic performance thereof is uncompromised. As noted above, these pulses then serve as triggers for 100 millisecond pulse stretchers described in FIG. 8 in connection with blocks 426 and 428. In the foregoing compilation of components of circuit 420, the inverters 530, 538, 550, 560, and 566 may be provided as type 74HC14 devices, while the NAND functions 546 and 556 may be provided as type 74HC10 devices. The type 74HC14 Schmitt-trigger inverters at 560 and 566 advantageously generate fast rise and fall times at lines 562 and 568.

Figure 11C:
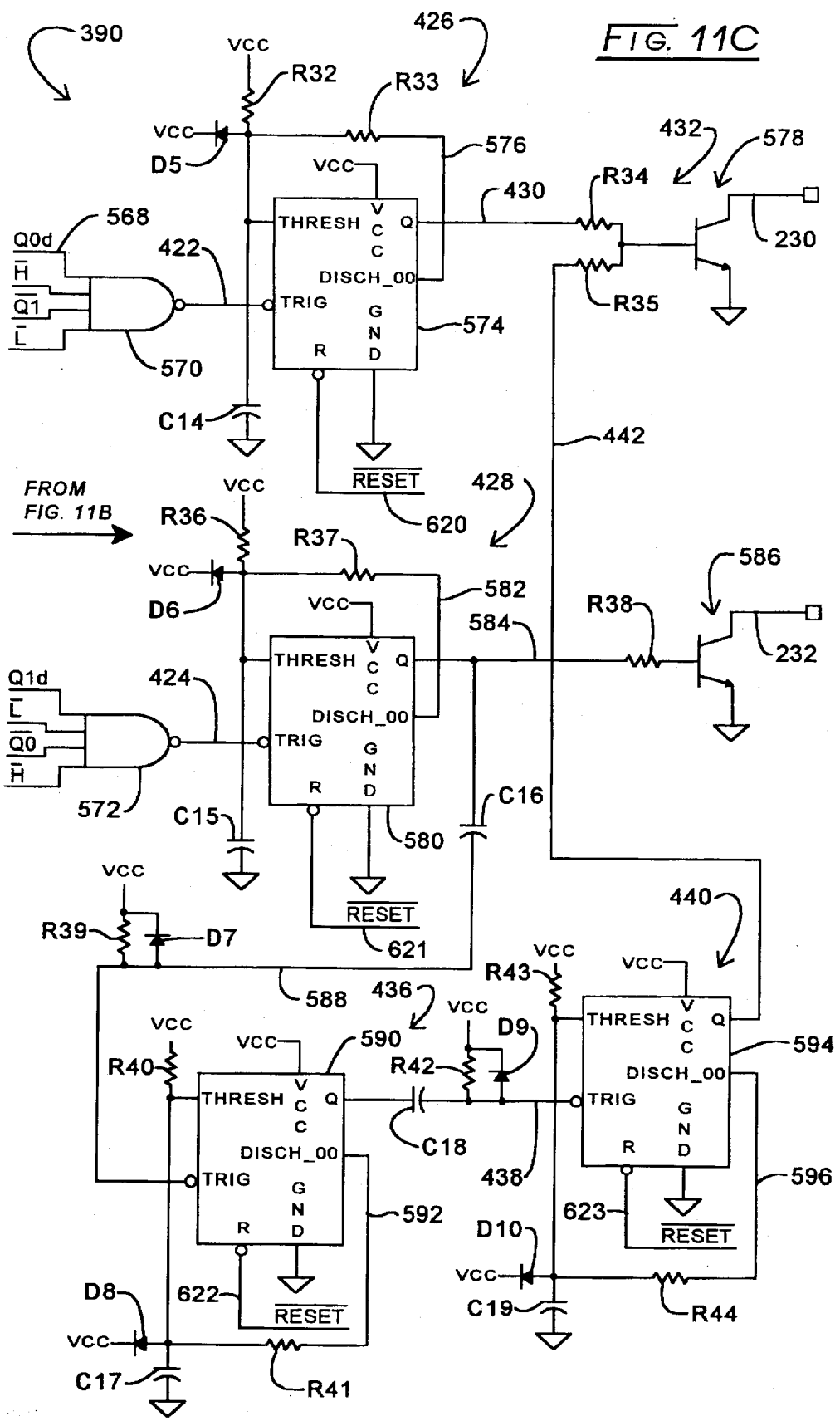

Referring to FIG. 11C, line 568 reappears carrying the Q0d signal which is directed to one input of a NAND function 570 whose output is earlier described at like 422. In addition to the signal at line 568, the remaining inputs to device 570 are as labeled, $\overline{H}$, $\overline{Q1}$, and $\overline{L}$. This provides the reset count output as described in conjunction with the above Boolean expression shown as equation (2). Correspondingly, a NAND device 572 is seen to provide an output at line 424 representing the squelch switch actuation at actuating surface 50 of probe 14 in response to the application of signals Q1d, $\overline{L}$, $\overline{Q0}$, and $\overline{H}$ as labeled on the inputs thereto. Devices 570 and 572 may be provided as type 74HC20.

The output at line 422 which occurs on the actuation of the reset count actuating surface 48 is directed to the trigger input of a monostable device 574 earlier described in conjunction with block 426 as "MONOSTABLE R.C.". Device 574 may be provided as a type ICM7556 timing device which performs in conjunction with an internally developed threshold. In this regard, the device is configured such that the trigger terminal is coupled to output line 422 while its threshold terminal is connected to an RC network comprised of capacitors C14 and resistor R32 coupled between Vcc and Found. The discharge terminal of device 574 is coupled via line 576 including resistor R33 and clamping diode D5 in a discharging relationship with the RC circuit comprised of resistor R32 and capacitor C14. Upon receipt of a trigger pulse from line 422, the previously discharged capacitor C14 will charge through resistor R32 to create a pulse of fixed duration, for example 100 ms at line 430 which is submitted through a resistive OR function formed of resistors R34 and R35 to the base of NPN transistor 578. Transistor 578 is wired across the reset count switch in control unit 12 and emulates its performance by pulling it down, inasmuch as the emitter of the device is coupled to Found. The presence of the switching signal at line 430 is at Vcc turning device 578 on, while the corresponding voltage at resistor R35 and line 442 is zero.

Monostable stage 428 includes a device 580 which is structured identically as that as 574. For example, the squelch signal at line 424 is directed to the trigger input thereof and its threshold terminal is coupled to an RC circuit including capacitor C15 and resistor R36. This RC circuit is coupled to the threshold terminal of device 580 and is discharge from line 582 which incorporates resistor R37 and diode D6. The resultant output which is provided at line 584, has a pulse of fixed predetermined duration, for example 100 milliseconds which is directed through base resistor R38 to the base of NPN transistor 586, the open collector configuring of which is connected across the squelch switching identified by a logic 1, in their absence, they are identified by a logic 0. It may be recalled that the signal "L" is produced by the actuation of either the reset count switch at actuating surface 48 or squelch switch at the actuating surface 50, while the "H" signal is asserted in response only to the probe mounted switch component associated with the squelch actuating surface 50. As defined by the state diagram, the two Mealy outputs will be present only during certain state transitions. In FIG. 10, the three stable states, a–c, are represented, respectively, by labeled circles 470–472. Resting state a at circle 470 is one where there is no pulse signal present from either of the comparators 400 or 401, and thus an $\overline{LH}/00$ condition obtains, and in the absence of some signal, as represented at transitional loop, that resting state a will remain. However, should a pulse commence, for example having been derived at lower threshold comparator 400, then as represented by transition arc 476, a transition is made to state b represented at circle 471. The condition $\overline{LH}/00$, if continuing or recurring, will cause the maintance of state b as represented by the transition loop 478. However, if the pulse output from comparator function 400 is provided without the presence of a signal The output of stage 436 is present at line 438 and is fed through capacitor C18 to the corresponding trigger terminal of device 594 of monostable stage 440. As before, line 438 is normally held to Vcc through pull-up resistor R42 about which is coupled protective diode D9. Thus, device 594 is triggered on the negation edge of the signal at line 438. Device 594 is identical to that at 574, the threshold terminal thereof being coupled to an RC circuit including capacitor C19 and resistor R43. This RC circuit is discharged from the discharge terminal of device 594 which, as before, is coupled thereto through line 596, resistor R44, and diode D10. The derived output of stage 440 is a pulse described in conjunction with FIG. 9 at 460 and is directed through ORing resistor R35 to transistor 578 to provide a count reset emulating pulse at line 230, which follows a squelch emulating pulse at line 230 by an interval established at stage 436.

Looking to FIG. 11D, the level 3 comparator stage 402 is revealed at a higher level of detail. Stage 402 includes a comparator device 598, the negative input terminal to which is coupled to receive the negative going signal at line 518 through capacitor C20. Device 598, as before, may be a type LF311 and provides an output at line 600. A regenerative feedback path is coupled to line 600 which includes line 602 along with resistors R45 and R46. Additionally, device 598 is configured with power decoupling capacitor C21. As before, the threshold for stage 402 is derived from a divider circuit including resistors R47 and R48 coupled between +12 v and ground, and a resistor R49. The values for these resistors are chosen to provide a relatively high upper limit, the intended purpose of this circuit being to inhibit the operation of the monostable devices under a large probe current draw, which phenomenon occurs when the probe 14 initially is plugged into a console 12 with the power on. Output line 600 is pulled up to Vcc through resistor R50 and is inverted at inverter 604, the output of which at line 606 is introduced to the trigger terminal of a pulse defining monostable device 608. Device 608 may be of the earlier type ICM7556 and provides an output at line 610 of duration determined by an RC circuit including capacitor C22 and resistor R51. This RC circuit is coupled to the threshold terminal of device 608 and is selectively discharged from the discharge terminal thereof in conjunction with line 612, resistor R52, and diode D11. The output at line 610 is inverted at an inverter 614 and provides a pulse output at line 418 carrying a $\overline{RESET}$ signal which is supplied simultaneously chart and assignment map wherein measurable variables are assigned to the arbitrary states a, b, and c. With such a map, variables Q0 and Q1 can be defined with their assignment to the noted states. Then, an excitation table may be developed with unique secondary states q1, q0. In this regard, the variable Q0 is only equal to q0 after a transition occurs and the same criteria applies with respect to variables Q1 and q1. This information can be transferred to Karnaugh maps and Boolean logic equations then may be developed. For example, the following four equations obtain for the circuit logic at hand:

$$Q1 = H + (L \cdot q1) \tag{1}$$

$$\text{Reset Count} = Q0d \, \overline{Q1} \, \overline{LH} \tag{2}$$

$$Q0 = L \, \overline{Hq1}; \text{ and} \tag{3}$$

$$\text{Squelch} = Q1d \, \overline{Q0} \overline{LH} \tag{4}$$

In the above equations, the variables Q0d and Q1d represent the stretched signals at the outputs of inverter stages 566 and 560, respectively, as described in connection with FIG. 11B.

a detector assembly coupled in sealed relationship to said housing at said forward end and including a crystal detector responsive to said emissions to provide corresponding detector outputs;

a piezoelectric switch actuable in response to said hand generated stress to derive switch signals having a pressure responsive surface and an oppositely disposed support surface positioned within said switch receiving channel, said pressure responsive surface being located in abutting adjacency with said switch contact surface;

a switch support assembly having first and second wedges exhibiting predetermined slopes and having respective mutually contacting abutting surfaces and first and second substantially parallel outer surfaces spaced apart a loading distance derived by relative positioning between said first and second abutting surfaces, said switch support assembly being positioned within said switch receiving channel intermediate said load surface and said piezoelectric switch support surface, said loading distance being selected to preload said piezoelectric switch against said switch contact surface; and a transmission assembly coupled with said housing at said rearward end for conveying signals corresponding with said detector outputs and said switch signals to an evaluation and control system.

2. The instrument of claim 1 in which:

said housing includes a detector signal channel extending rearwardly from said forward end; and said detector assembly includes a preamplifier circuit electrically coupled with said crystal detector and said transmission assembly and positioned to extend within said detector signal channel.

3. The instrument of claim 2 in which said detector signal channel is spaced from said switch receiving channel a distance defining a shield wall.

4. The instrument of claim 1 in which:

said housing extends along a longitudinal axis between said forward and rearward ends;

said switch receiving channel extends along said axis;

said housing includes a detector signal channel extending along said axis and spaced from said switch receiving channel a distance defining a shield wall; and said detector assembly includes a preamplifier circuit electrically coupled with said crystal detector and said transmission assembly and positioned to extend within said detector signal channel.

5. The instrument of claim 4 in which:

said detector assembly is mounted upon said housing at a predetermined angle with respect to said longitudinal axis; and said preamplifier is circuit board mounted and said circuit board is connected to and extends from said detector assembly into said detector signal channel.

6. The instrument of claim 4 in which:

said housing is cylindrical and includes a forward cavity extending inwardly from said forward end in communication with said switch receiving channel and said detector signal channel; and said first wedge first outer surface is attached to said piezoelectric switch support surface and extends into said forward cavity.

7. The instrument of claim 6 in which:

said housing includes a detector signal channel extending rearwardly from said forward end; and said detector assembly includes a preamplifier circuit electrically coupled with said crystal detector and said transmission assembly and positioned to extend within said detector signal channel.

8. The instrument of claim 7 in which said detector signal channel is spaced from said switch receiving channel a distance defining a shield wall.

9. The instrument of claim 8 in which:

said first and second piezoelectric switches generate respective first and second switch voltage signals upon the actuation thereof; and including first and second current deriving circuits mounted within said switch receiving channel and respectively responsive to said first and second switch voltage signals to derive respective first and second said switch signals at respective first and second current levels.

10. The instrument of claim 9 in which said housing includes a rearward cavity extending inwardly from said rearward end in communication with said switch receiving channel and said detector signal channel.

11. The instrument of claim 1 in which:

said housing is cylindrical and extends along a longitudinal axis;

first and second said piezoelectric switches are mounted within said switch receiving channel and are spaced apart a predetermined distance along said longitudinal axis;

said housing includes first and second said switch actuating surfaces spaced apart said predetermined distance and aligned with respective said first and second piezoelectric switches; and said first and second switch actuating surfaces being substantially flat, formed as an indenture within said housing surface and separated by a rib extending perpendicularly to said longitudinal axis.

12. The instrument of claim 11 in which said rib extends upwardly from said first and second switch actuating surfaces to a top surface located below said housing hand graspable surface.

13. The instrument of claim 1 in which said first and second wedges are substantially identically dimensioned.

14. The instrument of claim 13 in which said first and second wedge abutting surfaces are inclined at a said slope of about 2 degrees.

15. A system for detecting and locating a source of photon emissions emanating from tissue within a body, comprising:

a hand manipular probe including:

a housing with a hand graspable surface extending along an axis between forward and rearward ends having a switch receiving channel formed therein, said switch receiving channel extending along said axis, having a switch contact surface and an oppositely disposed load surface, a first switch actuating surface formed as an indentation into said housing hand grippable surface opposite said switch contact surface and spaced therefrom to define a predetermined switch wall thickness effective to inwardly transmit hand generated stress, and a detector signal channel extending along said axis;

a detector assembly coupled in sealed relationship to said housing at said forward end and including a crystal detector responsive to said emissions impinging thereon to provide corresponding detector outputs, an amplifier stage within said detector signal channel adjacent said detector, responsive to said detector outputs in the presence of an applied power supply to derive count outputs at an output line extending along said detector signal channel, device 580 is coupled to line 232 and the emitter thereof is coupled to ground.

Line 584 also is coupled by line 588 to the trigger terminal of monostable circuit 436 incorporating device 590 which is identical to device 574. It may be noted that the duration of the output pulse produced by monostable No. 1 (426) is approximately twice that at circuits 426 and 428. The pulse signal from line 584 is fed along line 588 through capacitor C16 to the trigger input of device 590. However, line 588 is coupled to Vcc through pull-up resistor R39 about which is connected a protective dime D7. As a consequence, device 590 is triggered on the negation edge of the pulse presented from line 588 in the manner described at 458 in FIG. 9. Stage 436 functions to provide a pulse delay between the generation of a squelch emulating signal at line 584 and the generation of a reset count emulating signal at line 442. Accordingly, the threshold terminal of device 590 is coupled to an RC circuit including resistor R40 and capacitor C17. This RC circuit is selectively discharged by the network coupled to the discharge terminal thereof including line 592, resistor R41, capacitor C17, and diode D8.

594 as represented at respective lines 620-623 in FIG. 11C.

Since certain changes may be made in the above-described method, system, and apparatus without departing from the scope of the invention herein involved, it is intended that all matter contained in the description thereof or shown in the accompany drawings shall be interpreted as illustrative and not in a limiting sense.

We claim:

1. An instrument for detecting and locating a source of radiation emissions emanating from tissue within a body comprising:

a housing with a hand graspable surface extending between forward and rearward ends, having a switch receiving channel formed therein, said switch receiving channel having a switch contact surface and an oppositely disposed load surface, at least one switch actuating surface formed into said housing hand grippable surface opposite said switch contact surface and spaced therefrom to define a predetermined switch wall thickness effective to inwardly transmit hand generated stress;

a piezoelectric switch actuable in response to hand generated stress to derive a switch voltage signal, having a pressure responsive surface and an oppositely disposed support surface, positioned within said switch receiving channel, said pressure responsive surface being located in abutting adjacency with said switch contact surface beneath said fast switch abutting surface, a current deriving circuit positioned within said switch receiving channel, having an output coupled with said applied power supply and responsive to said switch voltage signal to impose a current signal of predetermined amplitude at said applied power supply, a switch support assembly having fast and second wedges exhibiting predetermined slopes and having respective mutually contacting abutting surfaces and first and second substantially parallel outer surfaces spaced apart a loading distance derived by relative positioning between said first and second abutting surfaces, said switch support assembly being positioned within said switch receiving channel intermediate said load surface and said piezoelectric switch support surface, said loading distance being selected to preload said piezoelectric switch against said switch contact surface;

a control assembly located remotely from said probe, having at least one function selection switch actuable to derive a function input, a power supply network for deriving said applied power supply, an input network for receiving and evaluating said count outputs to derive count associated signals, an output component responsive to an applied output signal to generate a perceptible output, a processor responsive to said function input and said count associated outputs to derive a said output signal corresponding therewith, a monitoring amplifier stage responsive to current levels of said applied power supply for providing a monitor output corresponding therewith, and a level comparator circuit responsive to a said monitor output corresponding with the presence of said current signal to derive an emulating signal corresponding with said function input and effecting said processor derivation of said perceptible output; and an elongate flexible connector assembly coupled between said probe and said control assembly for coupling said output line with said input network and for conveying said applied power supply from said power supply network to said amplifier stage of said probe.

16. The system of claim 15 in which said flexible connector assembly is permanently connected in sealed relationship with said probe housing rearward end.

17. The instrument of claim 15 in which:

said housing includes a detector signal channel extending rearwardly from said forward end;

said detector assembly includes a preamplifier circuit electrically coupled with said crystal detector and said transmission assembly and positioned to extend within said detector signal channel.

18. The instrument of claim 15 in which:

said housing is cylindrical and includes a forward cavity extending inwardly from said forward end in communication with said switch receiving channel and said detector signal channel; and said first wedge first outer surface is attached to said piezoelectric switch support surface and extends into said forward cavity.

* * * * *